United States Patent [19]

Arisawa et al.

[11] Patent Number: 5,240,849

[45] Date of Patent: Aug. 31, 1993

[54] DNA CODING FOR ENZYME CAPABLE OF ACYLATING THE 4"-POSITION OF MACROLIDE ANTIBIOTIC

[75] Inventors: Akira Arisawa, Yokohama; Naoto Kawamura, Yamato; Ikuo Kojima, Kawasaki; Yasushi Okumura, Oiso; Kazuhiko Okamura, Fujisawa; Hiroshi Tone, Yokohama; Rokuro Okamoto, Fujisawa, all of Japan

[73] Assignee: Sanraku Incorporated, Tokyo, Japan

[21] Appl. No.: 356,323

[22] Filed: May 23, 1989

[30] Foreign Application Priority Data

May 24, 1988 [JP] Japan ................... 63-125091
Mar. 3, 1989 [JP] Japan ................... 1-50120

[51] Int. Cl.$^5$ .............. C12N 15/31; C12N 15/76; C12N 15/70
[52] U.S. Cl. .............. 435/252.33; 435/252.35; 435/320.1; 336/23.2; 935/11; 935/29; 935/73; 935/75
[58] Field of Search .............. 435/69.1, 172.1, 320.1, 435/252.3, 252.33, 252.35; 536/27

[56] References Cited

U.S. PATENT DOCUMENTS 4,201,843 5/1980 Okamoto et al. ............ 435/76
5,068,189 11/1991 Epp et al. ............ 435/183
5,098,837 3/1992 Beckmann et al. ............ 435/142.3

FOREIGN PATENT DOCUMENTS 0121328 10/1984 European Pat. Off. .
0238323 9/1987 European Pat. Off. .
0354641 2/1990 European Pat. Off. .

OTHER PUBLICATIONS

"Chem. Abst.", 103:32971 (Aug., 1985).
Epp et al., "Biol. Actinomycetes '88", 82–85 (1988).
"J. Antibiotics", vol. XXXIII (11), 1309–1315 (Nov., 1980).
Epp et al., "Gene", 85(2) 293–301 (Dec., 1989).
Omura et al., "J. Antibiotics", 28 401–433 (1975).
Okamoto et al., "J. Antibiotics", 32 542–544 (1979).
Epp et al., "Gene", 53 73–83 (1987).
Epp et al., "Abstracts of the Seventh International Symposium on Biology of Actinomycetes", S1b-2, 1988, Tokyo, Japan.

Primary Examiner—Robert A. Wax
Assistant Examiner—William W. Moore
Attorney, Agent, or Firm—Wenderoth, Lind & Ponack

[57] ABSTRACT

A DNA fragment containing acyB gene coding for an enzyme capable of acylating the 4"-position of a macrolide antibiotic, said DNA fragment being derived from a microorganism of the genus *Streptomyces*, having a size of about 3.1 kb and being characterized by the restriction endonuclease map shown in FIG. 1, and a DNA restriction fragment resulting from digestion with a restriction endonuclease; a recombinant DNA plasmid containing this DNA fragment; a microorganism transformed with this recombinant plasmid; and a process for producing a 4"-acylated macrolide antibiotic by using the transformant.

12 Claims, 21 Drawing Sheets

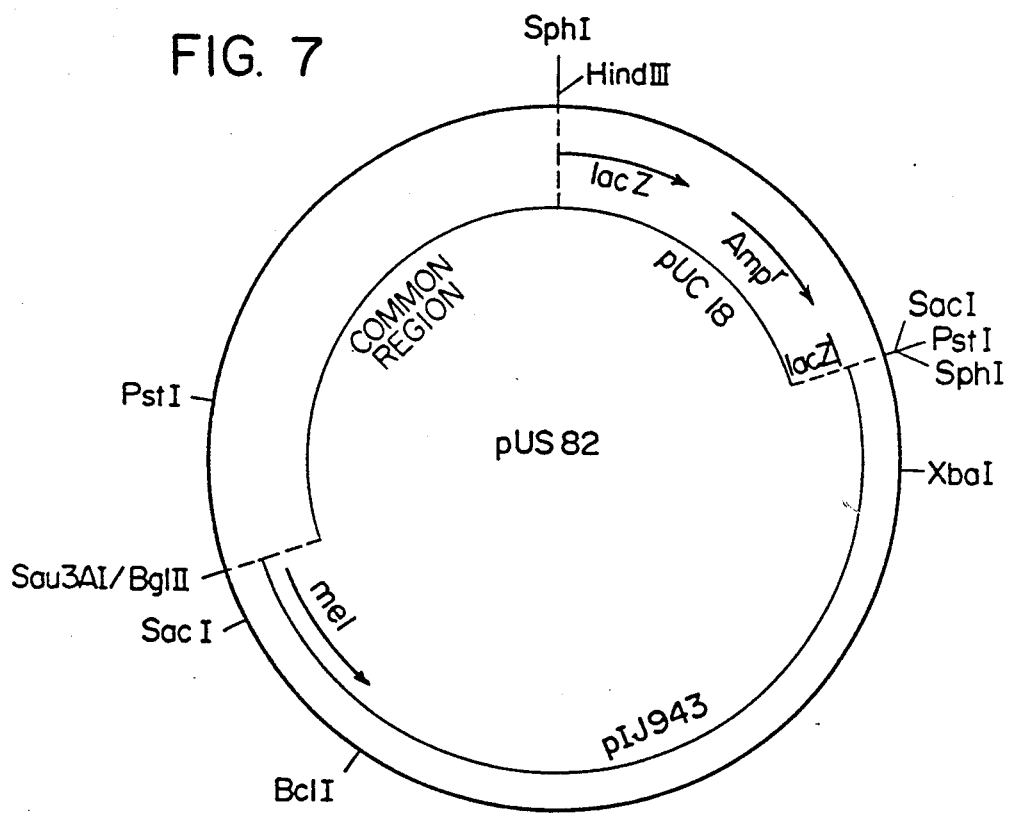
FIG. 7
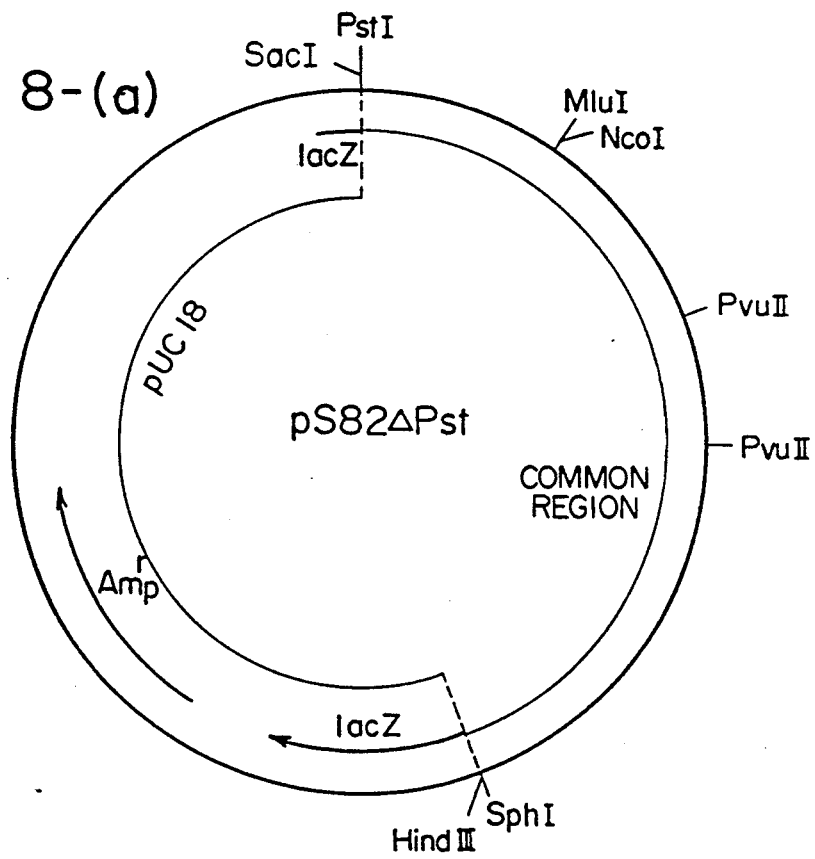
FIG. 8-(a)

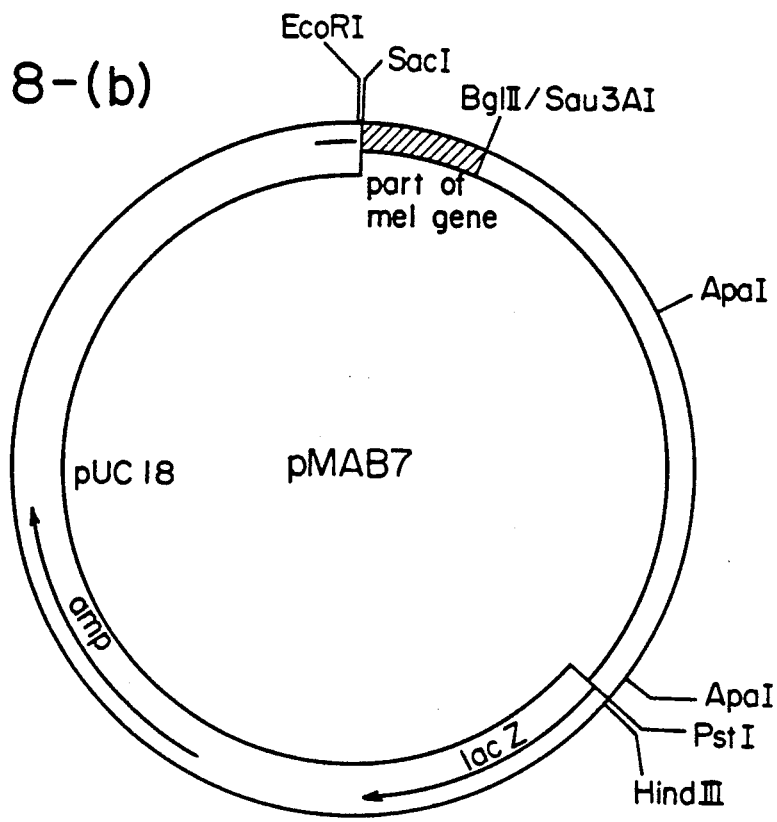
FIG. 8-(b)
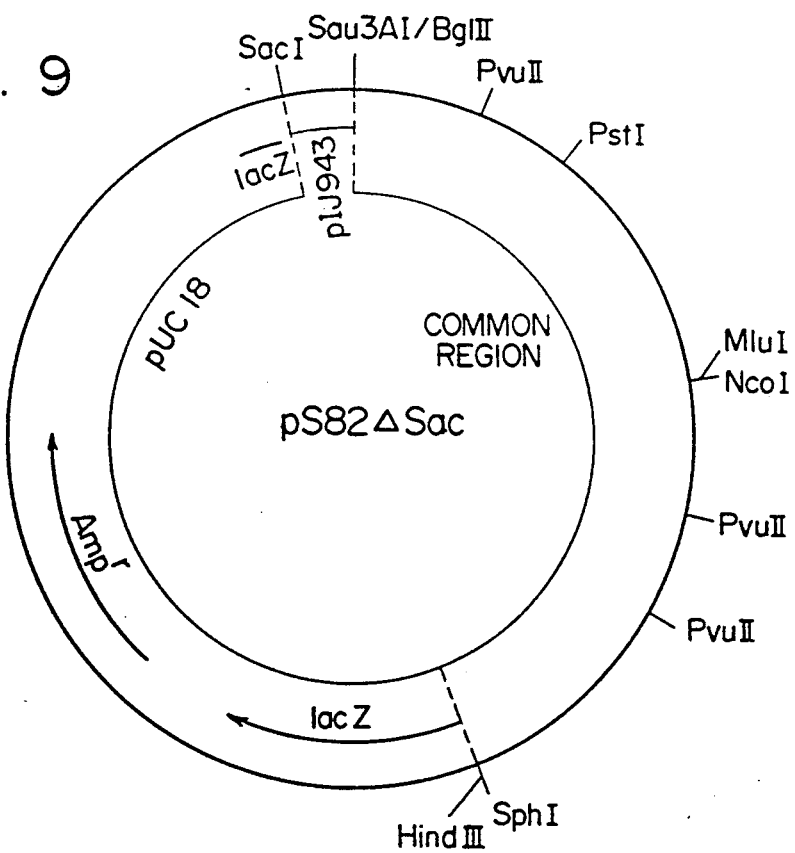
FIG. 9

2001
TACGGGTCT    GGCTCGCCTC
CGACGCCATG   TCGGCACCGG
TGAACTGGCA   TCTGACGCTG
GGCGGCGGAC   CGGGCGACCG
             2100
TCACGATCGG   CAGCTGAGCG
CGTACGGCGA   GGAGGAGAAG
CTCGTCGACC   TGGTGGCGGA
ACTCACGCGC   TCGAACCGGG
TGTTGGCGCG   TCCGGTGGTG
             2200
ATGGACGCGC   GGATCGCCAC
GCTGCCCCGG   CTGGTTCGGG
CGCTGTCCGC   GGCTGATCAA
TCGTTTCTCT   TAAGGGTGAG
CGGCGATCTT   CCGCTCGCCC
             2300
TCGCCGGCAG   CCGGGGCCAA
CTGGACAGGC   GCGCGCAGGT
CTGGCCCGCC   CAGCACCTCA
TGGAACAGCT   CAAGCGGCTC
AGGCGCCCTG   TGGAGTGGCA
             2400
GGGCTCCATC   AGCTTCGTCG

```
          10         20         30         40         50
ATGCCCCTGCCGAAACATCTTCCCGCGCTCGGCGGGATGCGTTTCATCTC
MetProLeuProLysHisLeuProAlaLeuGlyGlyMetArgPheIleSer
          60         70         80         90        100
CGCTCTACTGGTATTCACCTCCCATATATCGACACAGCCGTTCTTCAAGA
 AlaLeuLeuValPheThrSerHisIleSerThrGlnProPhePheLysAsn
         110        120        130        140        150
ACACCGAGATCAATTCCGCGCTGCAGTTCCCGCTGAACCGGCTGGGCCCG
  ThrGluIleAsnSerAlaLeuGlnPheProLeuAsnArgLeuGlyPro
         160        170        180        190        200
CTGACGGTCTCGTTCTTCTTCATGCTCAGCGGTTTCGTCCTCACCTGGGC
LeuThrValSerPhePhePheMetLeuSerGlyPheValLeuThrTrpAla
         210        220        230        240        250
GGGTCTGCCCGACAAGTCCAAGGTGAACTTCTGGCGGCGGCGCACGGTCC
GlyLeuProAspLysSerLysValAsnPheTrpArgArgArgThrValArg
         260        270        280        290        300
GCGCGTACTCGCTGCACCTGCCCGTGCTGCTGGTGACGCTGCTGATCGTG
 AlaTyrSerLeuHisLeuProValLeuLeuValThrLeuLeuIleVal
         310        320        330        340        350
CTGGCCCTCAACGAGCCCAACATGGGCCGATCGGTGTGGGACGGACTGCT
LeuAlaLeuAsnGluProAsnMetGlyArgSerValTrpAspGlyLeuLeu
         360        370        380        390        400
CACGAACCTGCTGCTGATCCAGGCATGGTTCCCCGACCACCACGAGTACG
 ThrAsnLeuLeuLeuIleGlnAlaTrpPheProAspHisHisGluTyrGly
         410        420        430        440        450
GCAGCATGAACCCGGTGGCGTGGTCGCTCTCCTGCGAGCTGTTCTTCTAC
 SerMetAsnProValAlaTrpSerLeuSerCysGluLeuPhePheTyr
         460        470        480        490        500
GCCATGTTCCCGTTCCTCTTCGCCTTCTTCACCAAGGTCCGTACGGACCG
AlaMetPheProPheLeuPheAlaPhePheThrLysValArgThrAspArg
```

FIG.11(a)-1

```
       510        520        530        540        550
GCTCTGGCGGTGGGCCGCCGCGGTGTCCGTGGCCGCCGTCTCCATCCCCC
 LeuTrpArgTrpAlaAlaAlaValSerValAlaAlaValSerIleProLeu
       560        570        580        590        600
TGGTCGCACTGCTGCTGCCGGCCAGCCCGCCCTGCCGTGGGACCCGGAC
 ValAlaLeuLeuLeuProAlaSerProProLeuProTrpAspProAsp
       610        620        630        640        650
ATGCCGCAGCTGCGGTGGTGGTTCATCTACATGTTCCCGCCGGTGCGGCT
 MetProGlnLeuArgTrpTrpPheIleTyrMetPheProProValArgLeu
       660        670        680        690        700
GCTGGAGTTCGTGCTCGGGATGCTCATGGCCCAGATCGTGATCCGGGGAC
 LeuGluPheValLeuGlyMetLeuMetAlaGlnIleValIleArgGlyArg
       710·       720        730        740        750
GCTGGAGGGGCCCGCGTCCCCTGGCCTGCGTCGCGCTGTTCTCAGCGGTG
 TrpArgGlyProArgProLeuAlaCysValAlaLeuPheSerAlaVal
       760        770        780        790        800
TTCGCGGTGACGTTCGCGGTGCCGAACCACTACGACCCCGGCGCGTTGAC
 PheAlaValThrPheAlaValProAsnHisTyrAspProGlyAlaLeuThr
       810        820        830        840        850
CGTCCCGGTGATCGCGCTGCTGCTCGCCTCGGTGGCCGTCGGTGATGTGC
 ValProValIleAlaLeuLeuLeuAlaSerValAlaValGlyAspValArg
       860        870        880        890        900
GCGGCGTCCGCTCCTGGCTGGGGACCAGGACGATGGTGCTGCTGGGGGAA
 GlyValArgSerTrpLeuGlyThrArgThrMetValLeuLeuGlyGlu
       910        920        930        940        950
CTCACCTTCGCCTTCTACCTCGTGCACTACCTGATCATCCAGTACGGGCA
 LeuThrPheAlaPheTyrLeuValHisTyrLeuIleIleGlnTyrGlyHis
       960        970        980        990       1000
CCGCTTCGCCGGCGGGAAGCAGGGCTATTACCGGCAGTGGGACACACCGG
 ArgPheAlaGlyGlyLysGlnGlyTyrTyrArgGlnTrpAspThrProAla
```

FIG. 11(a)-2

```
              1010       1020       1030       1040       1050
   CCGCCGTCGGGCTGACCCTGCTCGCCTTCACGCTGGCGCTGGGGCTGTCG
     AlaValGlyLeuThrLeuLeuAlaPheThrLeuAlaLeuGlyLeuSer
              1060       1070       1080       1090       1100

GCGTTCCTGCACTTCTTCGTGGAGAAGCCGGTCATGCGAACCCTGGGACG
     AlaPheLeuHisPhePheValGluLysProValMetArgThrLeuGlyArg
              1110       1120       1130       1140       1150

GCCGCGGCGGTCCCCGGACGCCGGCTCGACACCCAGGTCCGAACCCGCCC
     ProArgArgSerProAspAlaGlySerThrProArgSerGluProAlaPro
              1160

CGTCCGGCACTCCGTAG         FIG.11(a)-3
     SerGlyThrProTRM
```

```
         10        20        30        40        50
GTGCACAGTATTCCGTGTGGCTCAAAACCGTCGGCCTCCATGTGGGACAC
 MetHisSerIleProCysGlySerLysProSerAlaSerMetTrpAspThr
         60        70        80        90       100

CGGTGTCCATGACGACTTCGATACGCACATCTCCGAGACCTGCTCGGAGC
  GlyValHisAspAspPheAspThrHisIleSerGluThrCysSerGluLeu
        110       120       130       140       150

TGTTCAGTTCGCTGCGCCGGGCCGACCAGCGCAAGAGGGGCGAACAGTAC
   PheSerSerLeuArgArgAlaAspGlnArgLysArgGlyGluGlnTyr
        160       170       180       190       200

GTCCGTGGTCTGCTCACCGCTCAGGGACGCAAGACCGCCCGCAACCTCGC
 ValArgGlyLeuLeuThrAlaGlnGlyArgLysThrAlaArgAsnLeuAla
        210       220       230       240       250

CGCGTTCGTCGGTGAAGGCGCCGCGGACCAGAACCTCCACCACTTCGTGG
 AlaPheValGlyGluGlyAlaAlaAspGlnAsnLeuHisHisPheValAla
        260       270       280       290       300

CCGGATCCACCTGGGACTGGCGCTCCGTGCGTGCCGCGCTGGCCCGCTAC
  GlySerThrTrpAspTrpArgSerValArgAlaAlaLeuAlaArgTyr
        310       320       330       340       350

GCCGACCAGACGGTACGCGGGGACGCGTGGGTGATCCGCCCCATGGTGGT
 AlaAspGlnThrValArgGlyAspAlaTrpValIleArgProMetValVal
        360       370       380       390       400

CTACAAGGCAGGGGGACGGTCGGTCGGCGTGGGCCGGCGCTTCGTACCCG
  TyrLysAlaGlyGlyArgSerValGlyValGlyArgArgPheValProAsp
        410       420       430       440       450

ACCTGGGGCGGGTGGTCAGCTGTCAGCAGAGCTACGGGCTCTGGCTCGCC
 LeuGlyArgValValSerCysGlnGlnSerTyrGlyLeuTrpLeuAla
        460       470       480       490       500

TCCGACGCCATGTCGGCACCGGTGAACTGGCATCTGACGCTGGGCGGCGG
 SerAspAlaMetSerAlaProValAsnTrpHisLeuThrLeuGlyGlyGly
```

FIG. 11(b)-1

```
             510       520       530       540       550
        ACCGGGCGACCGTCACGATCGGCAGCTGAGCGCGTACGGCGAGGAGGAGA
         ProGlyAspArgHisAspArgGlnLeuSerAlaTyrGlyGluGluGluLys
             560       570       580       590       600
        AGCTCGTCGACCTGGTGGCGGAACTCACGCGCTCGAACCGGGTGTTGGCG
         LeuValAspLeuValAlaGluLeuThrArgSerAsnArgValLeuAla
             610       620       630       640       650
        CGTCCGGTGGTGATGGACGCGCGGATCGCCACGCTGCCCCGGCTGGTTCG
         ArgProValValMetAspAlaArgIleAlaThrLeuProArgLeuValArg
             660       670       680       690       700
        GGCGCTGTCCGCGGCTGATCAATCGTTTCTCTTAAGGGTGAGCGGCGATC
         AlaLeuSerAlaAlaAspGlnSerPheLeuLeuArgValSerGlyAspLeu
             710       720       730       740       750
        TTCCGCTCGCCCTCGCCGGCAGCCGGGGCCAACTGGACAGGCGCGCGCAG
         ProLeuAlaLeuAlaGlySerArgGlyGlnLeuAspArgArgAlaGln
             760       770       780       790       800
        GTCTGGCCCGCCCAGCACCTCATGGAACAGCTCAAGCGGCTCAGGCGCCC
         ValTrpProAlaGlnHisLeuMetGluGlnLeuLysArgLeuArgArgPro
             810       820       830       840       850
        TGTGGAGTGGCAGGGCTCCATCAGCTTCGTCGCCCCGTGCAACGTGGTGC
         ValGluTrpGlnGlySerIleSerPheValAlaProCysAsnValValLeu
             860       870       880       890       900
        TGACCGATCAGCTGCCGCAGCGCACGCTCCTGCTGTTCGGGGTGTGGCGC
         ThrAspGlnLeuProGlnArgThrLeuLeuLeuPheGlyValTrpArg
             910       920       930       940       950
        GCCAACCGCAGGCGACCCGCGGACCTGTGGCTCACCGACCTCACGTCCTG
         AlaAsnArgArgArgProAlaAspLeuTrpLeuThrAspLeuThrSerTrp
             960       970       980       990       1000
        GAACCGCGGCGCACTGCTGCGGCTGGCCATGCTGACCTGCCGCGTGGACG
         AsnArgGlyAlaLeuLeuArgLeuAlaMetLeuThrCysArgValAspAla
```

FIG.11(b)-2

```
            1010      1020      1030      1040      1050
CCGACTTCGCCCGCGTCAGCCTGGGCGTCGGCATCCGCGACTTCGAGGGC
  AspPheAlaArgValSerLeuGlyValGlyIleArgAspPheGluGly
    1060      1070      1080      1090      1100
CGCTCCTTCCAGGGCTGGCACCGTCACGTGACACTGGCCTCGATAGCCCA
  ArgSerPheGlnGlyTrpHisArgHisValThrLeuAlaSerIleAlaHis
    1110      1120      1130      1140      1150
CGCCCTACGCCTTTCCTGCACCGACACCGCCCGCACCCCCACGGCCCCGG
  AlaLeuArgLeuSerCysThrAspThrAlaArgThrProThrAlaProAla
    1160
CCCTGTCCCGCTGA
  LeuSerArgTRM
```

FIG. 11(b)-3

($^1$H-NMR of 4"-O-isovaleryltylosin)

($^1$H-NMR of 4''-O-acetyltylosin)

DNA CODING FOR ENZYME CAPABLE OF ACYLATING THE 4''-POSITION OF MACROLIDE ANTIBIOTIC

This invention relates to a DNA fragment containing a gene (named "acyB") which gives a host microorganism the enzyme activity of acylating the 4''-position of a macrolide antibiotic, a recombinant DNA plasmid containing this DNA fragment, a microorganism transformed with this recombinant plasmid, and a process for producing a 4''-acylated macrolide antibiotic by using the transformant.

Macrolide antibiotics (having 14-membered and 16-membered rings) are useful antibiotics which are widely used as pharmaceuticals for man and animals (for domestic animals and fish culture). S. Omura et al. [Journal of Antibiotics, vol. 28, pages 401-433 (1980)] and R. Okamoto et al. Journal of Antibiotics, vol. 27, pages 542-544 (1979)] reported that the antimicrobial activity of a 16-membered ring macrolide antibiotic is increased by acylation of the OH group at its 4''-position. In the paper of Okamoto et al., the 3- and 4''-positions of tylosin were acylated, and the pharmacological efficacies of the derivatives against various bacteria having resistance to macrolide antibiotics were examined; and it was concluded that 3- and 4''-acylated tylosins, particularly the 4''-acylated tylosins, have a higher pharmacological efficacy against these resistant bacteria than tylosin. However, the tylosin-producing microorganism strains produce only tylosin of the type in which —OH is attached to the 3- and 4''-positions. Acylation of —OH at these positions requires isolation of the tylosin and subsequent subjection of the isolated tylosin to a chemical or biological method, and no other suitable method has been available.

The present invention provides an industrially very useful method in which a microorganism strain capable of producing a 4''-acylation product of a macrolide antibiotic is obtained by a genetic engineering technique from a microorganism strain which inherently cannot directly produce the 4''-acylation product.

Some of the previously known macrolide antibiotics are shown below.

Formula 1: tylosin

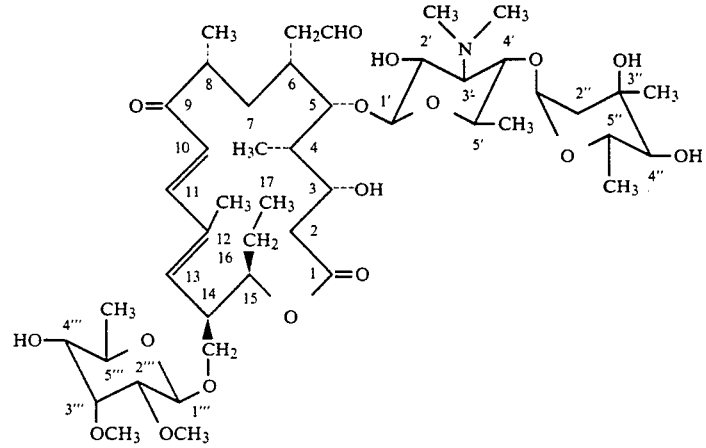

Formula 2: spiramycin

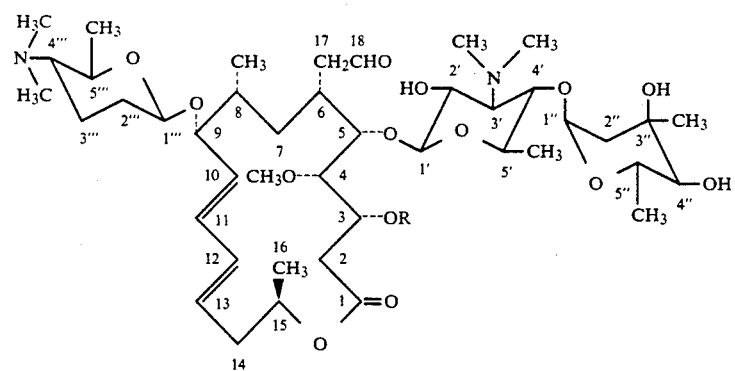

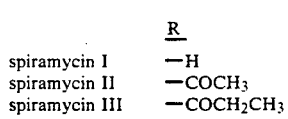

Formula 3: angoramycin

-continued

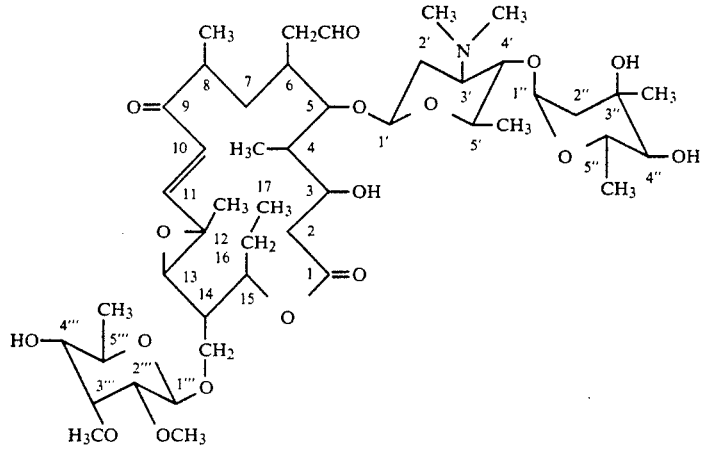

Formula 4: leucomycin

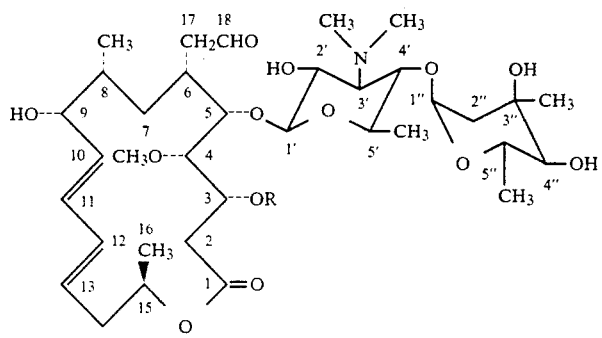

| | R |
|---|---|
| leucomycin U | —COCH$_3$ |
| leucomycin V | —H |

Formula 5: deltamycin X

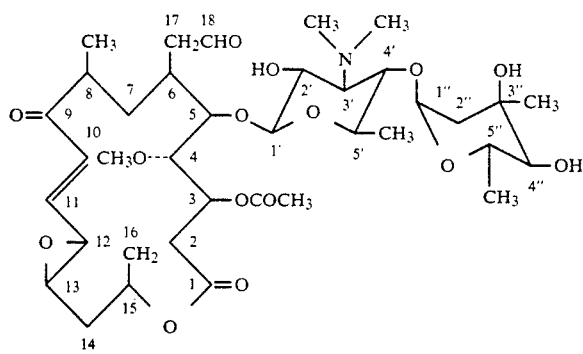

Chemical methods are generally employed for the acylation of the 4″-position of these macrolide antibiotics. Omura et al., however, reported that it was difficult to acylate a specific position in a molecule with good efficiency [Yakugaku Zasshi, vol. 106, pages 729-757 (1986)]. A biological method was proposed in Japanese Patent Publication No. 15160/1978. It is a method of acylating tylosin by using a microorganism having the ability to acylate tylosin, a culture of the microorganism, a treated product thereof, or an enzyme separated from the microorganism. According to this method, a macrolide antibiotic having —OH at the 3- and/or 4″-position is added as a substrate to cells, a culture or a cell extract of, for example, Streptomyces thermotolerans (ATCC 11416), Streptomyces hygroscopicus (ATCC 21582) or Streptomyces kitasatoensis (IFO 13686). However, the macrolide antibiotic-producing microorganism differs from the microorganism having acylating activity This is economically disadvantageous in industrial production.

To acylate biologically a macrolide antibiotic of the type having OH at the 3-position and/or 4″-position, a two-step operation is necessary in which the macrolide-producing microorganism strain is cultured and the macrolide antibiotic is isolated, and then the macrolide antibiotic substance is transformed with a microorganism having an acylating enzyme. In order to enable an acylated macrolide to be produced only by a macrolide-producing microorganism strain, much work has been done to provide a method which comprises isolating DNA of a macrolide acylating enzyme from a microorganism containing the macrolide acylating enzyme DNA, introducing the isolated DNA into a macrolide-producing microorganism strain by a genetic engineering technique, and causing the resulting microorganism strain to produce an acylated macrolide directly.

The recent advances in genetic engineering technique have made it possible to extract a desired DNA from a specific organism, and introduce the DNA into another desired microorganism either as such or after it is ligated with a suitable vector [D. A. Hopwood et al.: Genetic Manipulation of Streptomyces, The John Innes Foundation (1985)].

The present inventors made extensive investigations in order to isolate the DNA of an enzyme capable of acylating the 3- and/or 4"-position of a macrolide from a microorganism containing it, and consequently succeeded in isolating the 4"-position acylating enzyme gene acyB from a certain microorganism belonging to the genus Streptomyces. This has led to the accomplishment of the present invention.

The invention will be described partly with reference to the accompanying drawings, in which FIG. 1 is a restriction endonuclease map of a DNA fragment containing the gene acyB in accordance with this invention;

FIG. 7 is a map showing the restriction endonuclease cleavage sites and function of plasmid pUS82;

Figure 12:
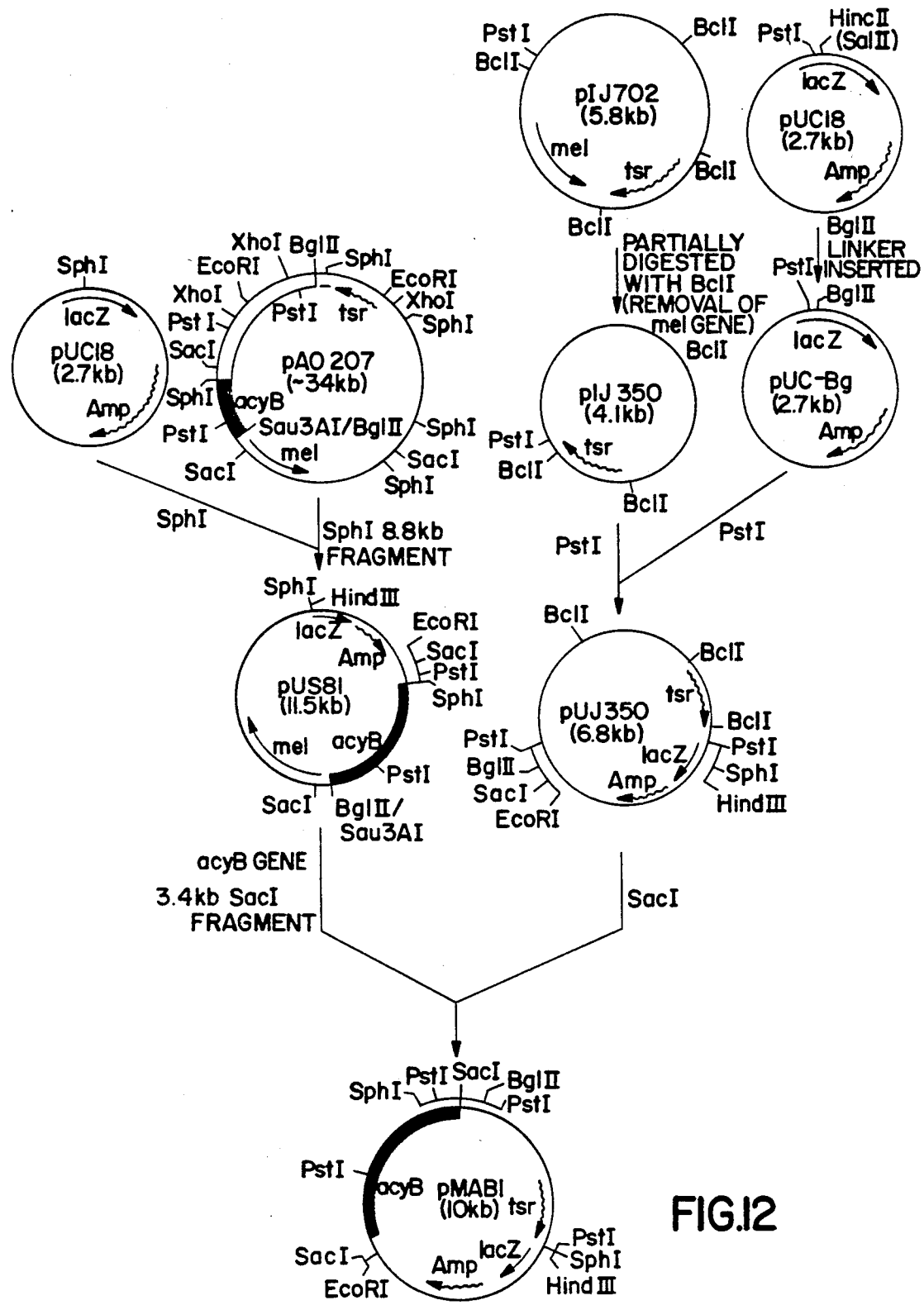
Figure 13:
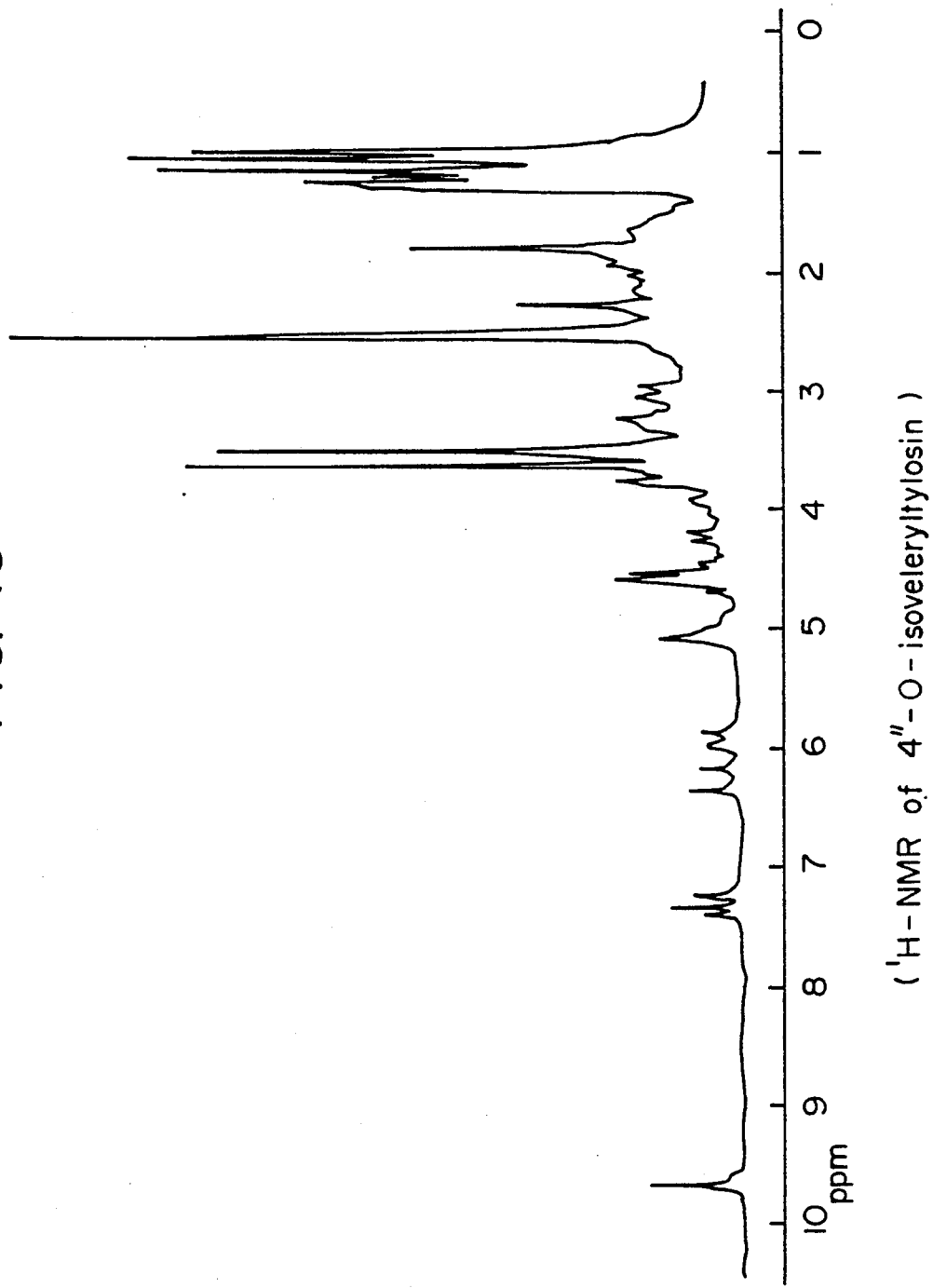

FIGS. 8-(a) and -(b) are maps showing the restriction endonuclease cleavage sites and functions of plasmid pS82ΔPst and plasmid pMAB7, respectively;

FIG. 9 is a map showing the endonuclease cleavage sites and function of plasmid pS82ΔSac;

FIG. 10 is the DNA base sequence of acyB;

FIGS. 11-(a) and -(b) are the base sequence and amino acid sequence of acyB1 and acyB2, respectively;

FIG. 12 is a view showing the process of constructing plasmid pMAB1;

FIG. 13 is a $^1$H-NMR chart of 4"-O-isovaleryl tylosin; and

Figure 14:
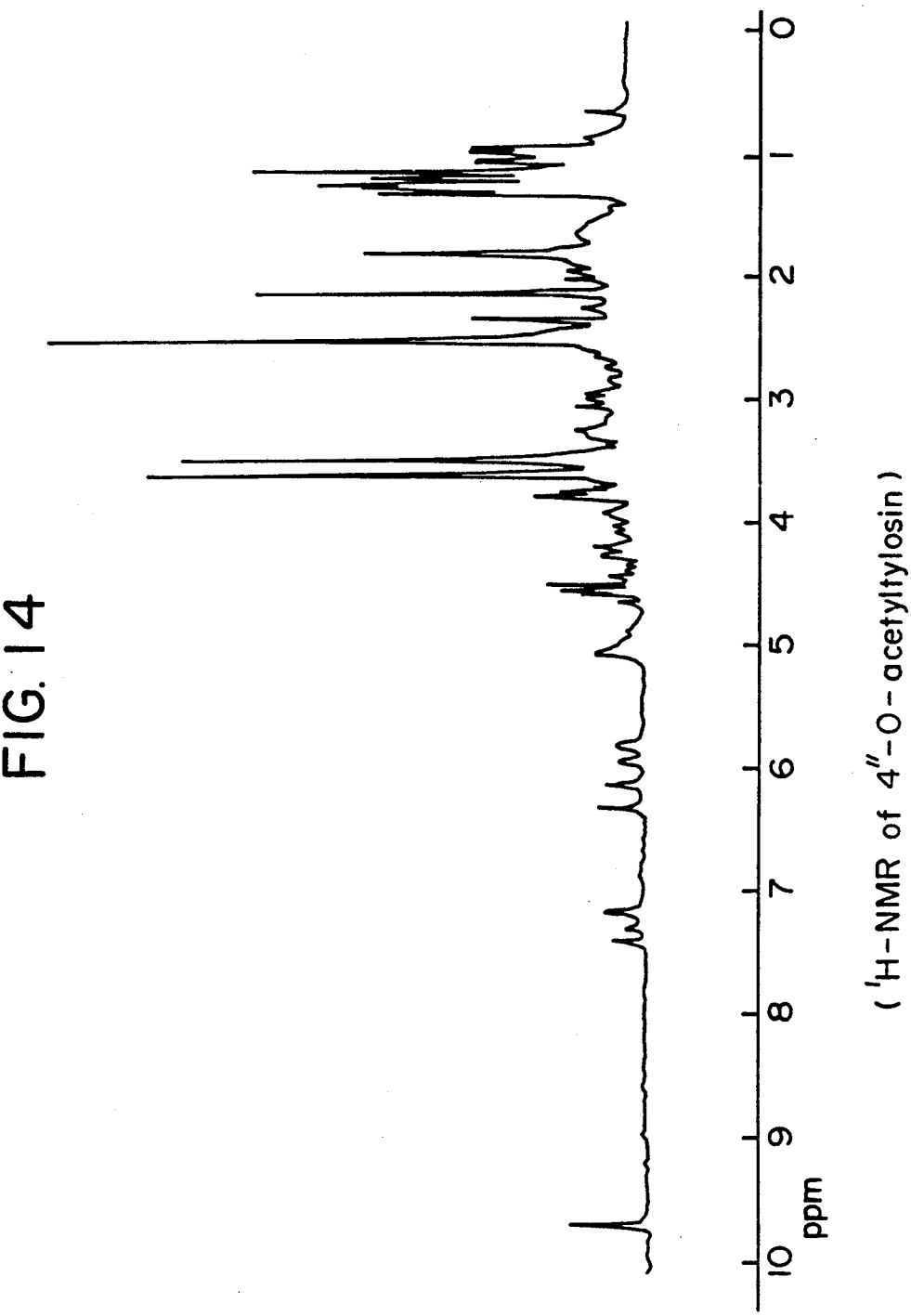

FIG. 14 is a $^1$H-NMR chart of 4"-O-acetyl tylosin.

Figure 1:
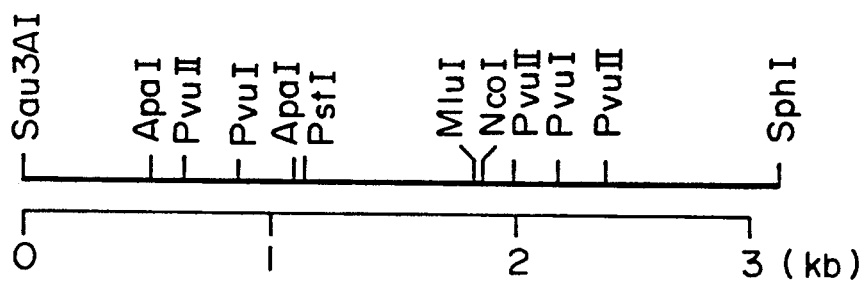

Thus, according to this invention, there are provided a DNA fragment containing an acyB gene encoding an enzyme capable of acylating the 4"-position of a macrolide antibiotic, said fragment being derived from a microorganism of the genus Streptomyces, having a size of about 3.1 kb and being characterized by the DNA base sequence shown in the restriction endonuclease map depicted in FIG. 1 of the accompanying drawings, and a DNA restriction fragments obtained by digesting the above DNA fragment with a restriction endonuclease.

The "DNA restriction fragments obtained by digesting the DNA fragment with restriction endonucleases", as used herein, denote DNA fragments of various sizes digested with restriction endonucleases to lengths necessary for expression of acylating enzyme activity. More specifically, said fragments are bound by the Sau-3AI-SphI restriction endonuclease sites shown in FIG. 1 which are capable of directing the expression of 4" acylase activity specific for the mycarose substituents of macrolide antibiotics of the genus Streptomyces.

The DNA fragment containing gene acyB and DNA restriction fragments in accordance with this invention are useful for commercial production of macrolide antibiotic derivatives such as 4"-acylated tylosin. They are particularly useful in that they make it possible to utilize the recombinant DNA technique commercially for microorganisms of the genus Streptomyces and other antibiotic-producing microorganisms.

The production and characteristics of the DNA fragment of the invention containing acyB gene, and the production of acylated macrolide antibiotics by using transformants obtained with the DNA fragment will be described in detail.

Microorganism strains belonging to the genus Streptomyces as sources of the DNA fragment containing gene acyB may be any microorganisms of the genus Streptomyces which have the ability to produce an enzyme capable of acylating the 4"-position of macrolide antibiotics. Examples include Streptomyces kitasatoenisis,
S. nabronensis var josamyceticus,
S. hygroscopicus,
S. platensis,
S. albireticuli,
S. cinerochromogenes,
S. djakartensis,
S. furdicidicus,
S. macrosporeus,
S. tendae,
S. thermotolerans, and
S. deltae;

Streptomyces thermotolerans is particularly suitable

The following description relates particularly to the case of using this preferred Streptomyces thermotolerans. It should be understood however that a gene coding for an enzyme capable of acylating the 4"-position of a macrolide can likewise be isolated from other microorganism strains of the genus Streptomyces.

Preparation of Genome DNA

S. thermotolerans is deposited, for example, at The American Type Culture Collection under the deposit No. ATCC 11416 and is easily available.

This microorganism is aerobically cultured at 28° C. as described in detail in Example 1 given hereinafter, and the cells in the logarithmic growth period were obtained The cells were treated in accordance with the method of Hopwood et al. (Genetic Manipulation of Streptomyces: A Laboratory Manual, The John Innes Foundation, Norwich, England, 1985) to prepare a genome DNA containing acyB gene.

Insertion of the DNA Fragment into a Vector Plasmid and Transformation

The resulting genomic DNA containing acyB gene is ligated with a suitable vector plasmid such as pIJ702, pIJ943, pIJ350 or pUC18.

As described in detail in Example 2 hereinbelow, the vector plasmid pIJ702 can be isolated from a microorganism containing it by phenol extraction and density gradient ultracentrifugation using cesium chloride. The resulting plasmid pIJ702 is digested with restriction endonuclease BalII. The DNA fragment obtained by partially digesting the above genomic DNA with restriction endonuclease Sau3AI is inserted into the resulting digested plasmid.

*Streptomyces lividans* TK24 is transformed with the resulting plasmid containing part of the genomic DNA of *Streptomyces thermotolerans* ATCC 11416 to obtain transformants which have acquired tylosin acylating ability (for details, see Example 3 given hereinafter). By extracting and purifying the plasmid from the transformants having tylosin acylating ability, plasmid pAOY-17 containing a DNA inserted fragment having a size of about 6 kb can be obtained.

In the same way as in the preparation of the plasmid pAOY-17, plasmid pAO207 can be obtained in which an about 13 kb restriction endonuclease Sau3AI digested fragment derived from *Streptomyces thermotolerans* is inserted into the restriction endonuclease BglII-cleaved site of plasmid pIJ943 (see Example 4 given hereinafter).

Figure 2:
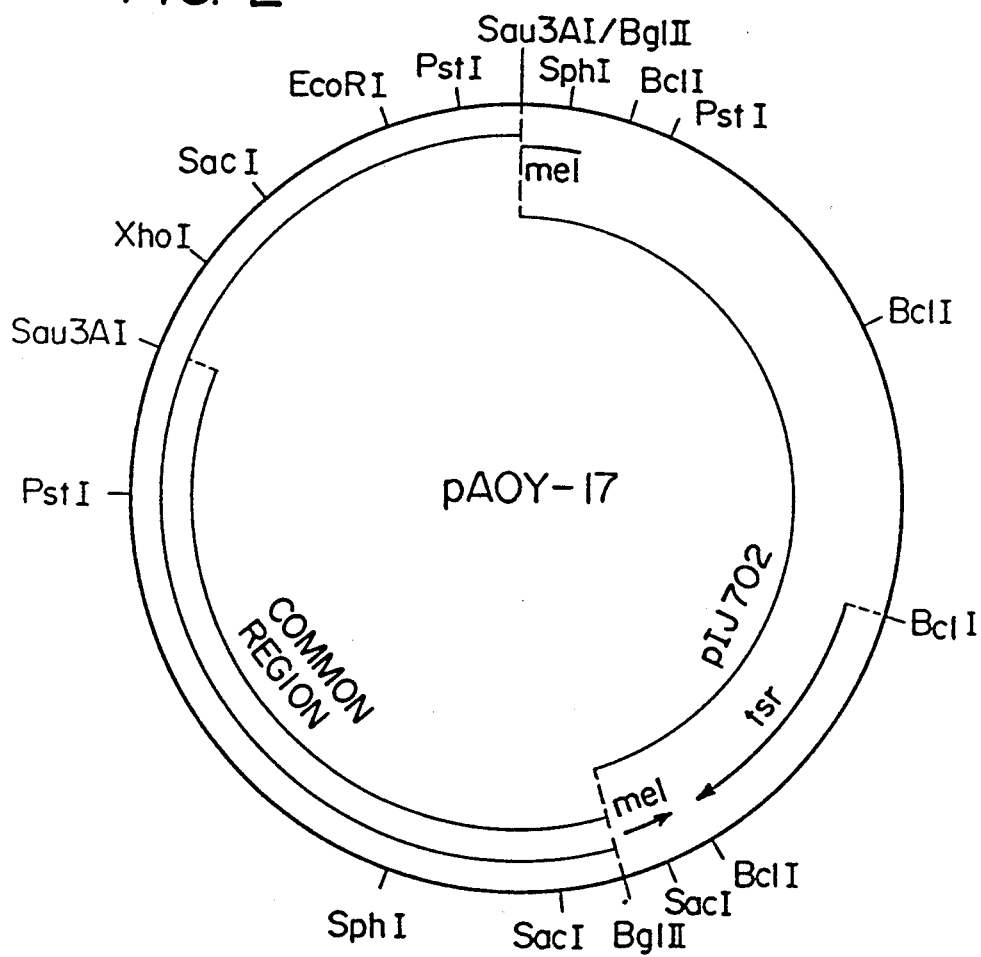
FIG. 2 is a map showing the restriction endonuclease cleavage sites and function of plasmid pAOY-17.
Figure 3:
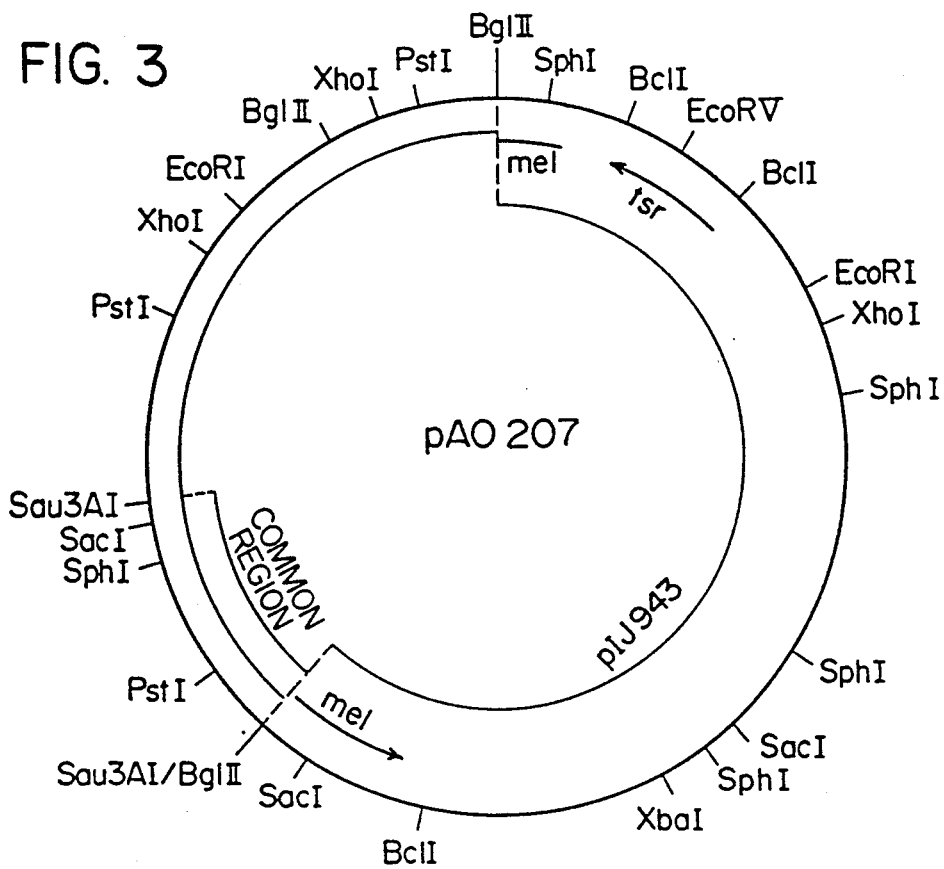
FIG. 3 is a map showing the restriction endonuclease cleavage sites and function of plasmid pAO207.

Plasmid pIJ702 is available from The American Type Culture Collection under deposit No. ATCC 35287. Plasmid pIJ943 is disclosed by Hopwood et al. see Genetic Manipulation of Streptomyces: A Laboratory Manual, pages 314–315, 1985, The John Innes Foundation], and may be obtained under *Streptomyces lividans* TK24/pIJ943 from The John Innes *Streptomyces* Culture Collection, The John Innes Institute, Colney Lane, Norwich NR4 7UH, England. *Streptomyces lividans* TK24, its host organism, may likewise be obtained from The John Innes *Streptomyces* Culture Collection. Maps showing the restriction endonuclease cleavage sites and functions of plasmid pAOY-17 and pAO207 are shown in FIGS. 2 and 3 of the accompanying drawings.

The *acy*B gene of the DNA fragment inserted into plasmids pAOY-17 and pAO207 can be further restricted. Specifically, the inserted DNA fragment is digested with a suitable restriction endonuclease, such as BglII, SacI and PstI to form a smaller DNA fragment, and the smaller DNA fragment is inserted into a suitable plasmid for the genus *Streptomyces*. *Streptomyces lividans* TK24 is transformed with the plasmid having inserted thereinto the smaller DNA fragment, and the ability of the transformant to acylate the 4"-position of tylosin to determine whether the inserted DNA fragment contains the *acy*B gene (see Example 7 below for details).

Thus, the *acy*B gene in the DNA fragment inserted in the plasmids pAOY-17 and pAO207 can be restricted as shown in FIG. 1. This DNA fragment is contained in the common DNA region present in the plasmid pAOY-17 and pAO207.

Homology of the Inserted DNA Fragment with the Genome DNA

To analyze the origin of the DNA fragment inserted into the plasmid pAOY-17 and pAO207, a 13 kb PvuII-cleaved fragment is labelled with dCTP, and subjected to Southern hybridization with the genomic DNA of *Streptomyces thermotolerans* ATCC 11416 or *Streptomyces lividans* TK24. The Southern hybridization is disclosed by Southern in Journal of Molecular Biology, vol. 98, page 503, 1975. This has led to the determination that the DNA fragments inserted into pAOY-17 and pAO207 are derived from *S. thermotolerans* ATCC 11416.

Construction of a Plasmid Having Inserted Thereinto the DNA Restricted Fragment Containing *acy*B, Gene The above plasmids pAOY-17 and pAO207 contain a *Streptomyces* replicon, a restriction fragment which imparts enzyme activity of acylating the 4"-position of tylosin, and as a selection marker, a thiostreptonresistant gene. The two plasmids can be utilized as useful starting substances for many plasmids of the invention containing *acy*B gene.

Figure 4:
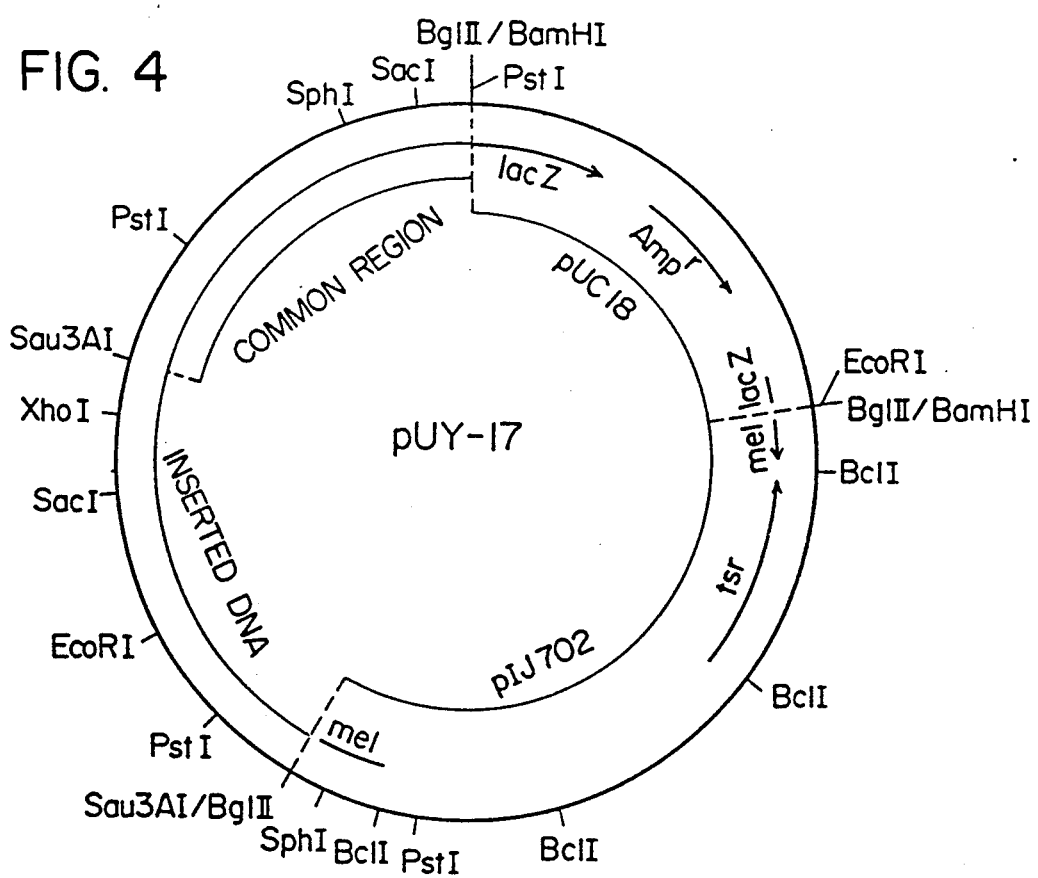
FIG. 4 is a map showing the restriction endounclease cleavage sites and function of plasmid pUY-17.

Proliferation of plasmids derived from *Streptomyces* is more rapid and efficient than that of plasmids derived from *Escherichia coli*. It is advantageous therefore to introduce a DNA restriction fragment containing the *acy*B gene into a plasmid from *Escherichia coli* such as pBR322 and pUC18, and replicate the fragment in *Escherichia coli*. By inserting a DNA restriction fragment containing *acy*B gene into plasmid pUC18 by the procedures described in Examples 5 and 6 given hereinbelow, plasmids pUY-17, pY-17ΔEco, pUS81, pUS82, pS82ΔPst, or pS82ΔSac can be prepared A commercial product is conveniently used as plasmid pUC18 (such as the one produced by Pharmacia). Maps showing the restriction endonuclease cleavage sites and functions of the above plasmids are shown in FIGS. 4 and g of the accompanying drawings.

pUY-17 has both a replicon of *Escherichia coli* and a replicon of genus Streptomyces, and can transform *Streptomyces lividans* to impart the ability to acylate the 4"-position of tylosin. The above plasmids except the pS82ΔPst completely retain the *acy*B gene. But in plasmid pS82ΔPst, part of the *acy*B-gene is deleted. Restriction fragments containing the *acy*B gene can be cut out from the above plasmids completely retaining the *acy*B gene by using restriction endonucleases such as SphI and SacI. The resulting restriction fragments can be inserted into such plasmids as pIJ702, pIJ943 and pIJ350 [Kieser et al.: Molecular and General Genetics, vol. 185, pages 223–238 (1982)]. The recombinant plasmids can transform *Streptomyces lividans* TK24 and impart to it the ability to acylate the 4"-position of a macrolide antibiotic.

The DNA fragments containing the *acy*B gene which are used for constructing plasmids in this invention may usually be modified in order to facilitate ligation. For example, the DNA fragment containing the *acy*B gene may be bound to a synthetic linker. Thus, a site specific for the subsequent ligation reaction can be constructed conveniently.

pIJ702, pIJ943, pIJ350 and pUC18 may be cited as examples of vector plasmids that can be used to introduce the DNA fragment containing the *acy*B gene of this invention into host microorganisms, but these specific examples are not limitative. For example, vector plasmids containing *Streptomyces* replicons or *Escherichia coli* replicons which are known to be useful equivalently in various host ranges may also be utilized. Part of the above plasmids may be utilized as a vector so long as the function of the replicon is not destroyed

Determination of the Base Sequence of the *acy*B Gene-Containing Fragment

By using plasmids having part or the whole of the *acy*B gene-containing fragment, such as pS82ΔSac or pS82ΔPst as a template DNA, the DNA base sequence of the *acy*B gene can be determined by the dideoxy chain termination method [F. Sanger et al.: Proc. Nat. Acad. Sci., vol. 74, pages 5463–5467 (1977)]. In accordance with this method, a base sequence composed of 2749 bases beginning with G of the sequence GATC at the Sau3AI, one end of the acyB gene-containing fragment on plasmid pS82ΔSac can be determined as shown in FIG. 10. By examining the determined base sequence for open reading frames, the translation region of the acyB gene is determined, and the amino acid sequence of an enzyme capable of acylating the 4"-position of a macrolide antibiotic encoded by the translation region of the acyB gene can be anticipated. By this procedure, two open reading frames going in two opposite directions from the base sequence shown in FIG. 10, namely going outwardly from the central part of the sequence, are discovered. The amino acid sequence of the upstream reading frame is shown in FIG. 11-(a) as acyB1, and the amino acid sequence of the downstream reading frame is shown in FIG. 11-(b) as acyB2.

Utility of the DNA Restriction Fragment Containing the acyB Gene

The DNA restriction fragment containing the acyB enzyme gene capable of acylating the 4"-position of a macrolide antibiotic has a wide range of utility.

The DNA fragment of this invention can be inserted into a vector plasmid, and introduced into a microorganism of the genus Streptomyces and a related microorganism. The restricting transformant is cultured, and by using the cultured cells, or the culture medium, or a treated product thereof, an enzyme capable of acylating the 4"-position of a macrolide antibiotic, or a material containing the enzyme, a 4"-acylated macrolide antibiotic can be produced.

It is also possible to prepare a probe by using part of the DNA fragment of the invention, and thus provide an effective means for screening genes related to the acyB gene.

An enzyme capable of acylating the 4"-position of a macrolide antibiotic, which is expressed by using the acyB gene of this invention is especially useful for acylating the 4"-position of tylosin. It has the ability to acylate the 4"-positions of other macrolide antibiotics such as spiramycin, angoramycin, leucomycin and deltamycin.

Accordingly, if a plasmid having the acyB gene of the invention inserted thereinto is introduced into a microorganism having the ability to produce a macrolide antibiotic, a 4"-acylated macrolide antibiotic can be directly produced. It is also possible to introduce such a recombinant plasmid into microorganisms which do not produce macrolide antibiotics. If the transformants are cultured in a medium containing a macrolide antibiotic, a 4"-acylated macrolide antibiotic can be produced.

The 4"-acylating enzyme produced by the transformants can of course be used as a catalyst for an enzyme reaction between the macrolide antibiotic and an acylating agent.

Transformation of a Plasmid Having Inserted Thereinto the DNA Restriction Fragment Containing the acyB Gene A plasmid having inserted thereinto the acyB gene can be introduced into suitable host microorganisms according to the vector plasmid The host microorganism may be those having the ability to produce macrolide antibiotics or those which do not produce macrolide antibiotics. Examples of the host organisms that can be used in this invention include Streptomyces kitasatoensis, S. narbonensis var josamyceticus,,S. ,hygroscopicus, S. platensis, S. albireticuli, S. cinerochromogenes, S. djakartensis, S. macrosporeus, S tendae, S. deltae, S. fradiae, S. eurythermus, S. ambofaciens, S. kasugaensis, S. erythreus and S. kanamyceticus.

Generally, however, macrolide antibiotic-producing microorganisms substantially incapable of producing an enzyme capable of acylating the 4"-position of a macrolide antibiotic, such as S. eurythermus ATCC 14975 (a microorganism producing angforamycin), and S. fradiae ATCC 19609 (a microorganism producing tylosin) z0 f are suitable, particularly the latter.

The transformation of these host organisms with the recombinant plasmids containing the acyB gene can be performed by methods known per se, for example the method described in Genetic Manipulation of Streptomyces: A Laboratory Manual, 1985, The John Innes Institute.

By culturing the resulting transformants in a medium containing a macrolide antibiotic, a 4"-acylated macrolide antibiotic can be formed. A transformant having the ability to produce a macrolide antibiotic may be acylated at the 4"-position by culturing it in a medium free from a macrolide antibiotic.

A 4"-acylated macrolide antibiotic can also be produced by culturing the transformant and reacting the macrolide antibiotic with an acylating agent, such as acetyl coenzyme A, propionyl coenzyme A, n-butyryl coenzyme A, isovaleryl coenzyme A, phenylacetyl coenzyme A, or a biosynthesis precursor for donating an acyl group, such as leucine, in the presence of the cultured cells or a treated product thereof such as a cell-free extract obtained by disrupting the cultured cells by ultrasonic treatment.

Thus, according to this invention, there can be produced macrolide antibiotics in which the 4"-position is acylated with an alkanoyl group having 1 to 5 carbon atoms, such as acetyl, propionyl, n-butyryl or isovaleryl group, for example 4"-acetyltylosin, 4"-propionyltylosin, 4"-n-butyryltylosin, 4"-isovaleryltylosin, 4"-acetylangoramycin, 4"-propionylangoramycin, 4"-n-butyrylangoramycin, 4"-isovalerylangoramycin, 4"-acetylspiramycin, 4"-propionylspiramycin, 4"-n-butyrylspiramycin, and 4"-isovalerylspiramycin.

Culturing of the Transformant

A host microorganism, for example, a microorganism of the genus Streptomyces, transformed with a plasmid bearing the DNA fragment containing acyB gene of this invention by many methods using some different media.

Preferred carbon sources to be added to the culture medium include, for example, molasses, glucose, starch, oils and fats and glycerol. Suitable nitrogen sources include, for example, soybean meal, amino acid mixtures, dry yeasts and peptone. Nutrient inorganic salts may also be added to the medium. They include ordinary salts capable of releasing potassium, sodium, magnesium, calcium, phosphate, chlorine, sulfate ions, etc. Trace components such as vitamins may also be added as required. These trace components can be usually fed as impurities incidental to the addition of the other components. A macrolide antibiotic to be acylated may also be added as required.

The transformed microorganism of the genus Streptomyces can be cultured in a medium at a broad pH range of from about 5 to 9 at a temperature of about 20° to 40° C. under aerobic conditions. At this time, a condition necessary for maintaining the stability of the plasmid may be introduced For example, a drug such as thiostrepton may be added as a selective pressure.

The following examples illustrate the present invention in greater detail These examples are merely for illustrating the present invention, and are not intended to limit the scope of the invention.

EXAMPLE 1

Preparation of the Genomic DNA of *Streptomyces Thermotolerans* ATCC 11416

(A) Cultivation of *Streptomyces thermotolerans* ATCC 11416

One loopful of the above-identified microorganism cultured at 38° C. for 2 weeks was inoculated in 25 ml of a seed culture medium composed of 2% of soluble starch, 2% of soybean meal, 0.1% of yeast extract, 0.1% of K and 0.05% of $MgSO_4 \cdot 7H_2O$. The seed culture medium had been sterilized at 120° C. for 15 minutes in a 250 ml Erlenmeyer flask. The flask containing the seed culture in which the above microorganism was inoculated was shaken at 38° C. for 48 hours to form a seed. One milliliter of the seed was inoculated in 25 ml of a TSB medium (tryptic soy broth), and then cultured at 28° C. for 48 hours. The TSB medium was obtained from Difco Laboratories, Detroit, Mich., U. S. A. and adjusted to a concentration of 30 g/liter.

(B) Preparation of a Genomic DNA

The cells were collected and washed once with a 0.3% sucrose solution. Then, 5 ml, per gram of the cells, of 25% sucrose/Tris-HCl (50 mM, pH 8) was added. The cells were well dispersed and then the suspension was well mixed with a 10 mg/ml solution of lysozyme (grade 1, produced by Sigma Chemical Co.). The mixture was incubated at 30° C. for 30 minutes Subsequently, 0.6 ml of an EDTA solution (0.5M, pH 8) and 4.1 ml of a 10 mg/ml solution of pronase E (a product of Sigma Chemical Co.) were added, and the mixture was incubated at 30° C. for 5 minutes. Then, 3.6 ml of a 3.3% SDS (a product of Sigma Chemical Co.) solution was added and the mixture was incubated at 37° C. for 1 hour. Six milliliters of a phenol layer obtained by mixing 500 g of phenol and 500 g of chloroform with 200 ml of Tris-HCl (50 mM, pH 8)/NaCl (100 mM)/EDTA (5 mM, pH 8) was added, and mixed well under mild conditions. Thereafter, the solution was centrifuged (10,000 rpm, 20 minutes) to perform layer separation. About 7 ml of an aqueous layer was obtained. Two milliliters of chloroform was added to the aqueous layer, and they were well mixed under mild conditions. The mixture was then centrifuged (10,000 rpm, 10 minutes) to obtain about 7 ml of an aqueous layer. A 10 mg/ml solution of 30 microliters of ribonuclease A type 1-AS (a product of Sigma Chemical Co.) was heat-treated at 90° C. for 10 minutes, and added to the aqueous layer, and the mixture was incubated at 37° C. for 1 hour. 0.1 Volume of a sodium acetate solution (3M, pH 4.8) and 1 volume of isopropanol were added and well mixed. The mixture was left to stand at room temperature for 10 minutes, and centrifuged (6,000 rpm, 10 minutes). The precipitates were collected and dissolved in 5 ml of a TE buffer [Tris-HCl (10 mM, pH 8)/EDTA (1 mM, pH 8)], and then the solution was well mixed with 0.5 ml of a sodium acetate solution and 12.1 ml of ethanol. The mixture was left to stand overnight at −20° C. The precipitates were collected by centrifugation (6,000 rpm, 10 minutes) and vacuum dried in a desiccator. About 800 micrograms of genome DNA was obtained from 25 ml of the culture broth.

EXAMPLE 2

(A) Preparation of pIJ702

About spores of *Streptomyces lividans* ATCC 35287 were inoculated in 500 ml of a YEME + 34% sucrose medium containing 5 micrograms/ml of thiopeptin (*) (comprising 0.3% of yeast extract, 0.5% of bactopeptone, 0.3% of malt extract, 1% of glucose and 34% of sucrose; after sterilization, 1 ml of 2.5M $MgCl_2$ solution was added), and cultured under shaking at 28° C. for 48 hours.

(*) thiopeptin (prepared by extracting Thiofeed, a product of Fujisawa Pharmaceutical Industry Co., Ltd. with chloroform) was used as a selective pressure instead of thiostrepton [S. Pastka and J. W. Boldley, Antibiotics III, pages 551 to 573, 1975, Springer-Verlag].

The cells were collected, washed once with a 10.3% solution of sucrose, and then suspended in 45 ml of a 10.3% sucrose/Tris-HCl (25 mM, pH 8)/EDTA (21 mM, pH 8) solution. Five milliliters of a lysozyme solution (10 mg/ml, dissolved in the same solution as used in suspending the cells) and 250 microliters of a ribonuclease type 1-AS solution were added, and well mixed. The mixture was incubated at 37° C. for 30 minutes, then well mixed with 30 ml of 0.3 M NaOH/2% SDS solution and further incubated at 55° C. for 15 minutes. Twenty milliliters of the same phenol solution as used in Example 1 was added and well mixed, and then centrifugally separated (15,000 rpm, 15 minutes) to give about 70 ml of an aqueous layer. The aqueous layer was well mixed with 7 ml of a sodium acetate solution (3M, pH not adjusted) and 70 ml of isopropanol. The mixture was left to stand at room temperature for 10 minutes. The precipitates were collected by centrifugation (15,000 rpm, 15 minutes), and dissolved in 10 ml of TNE buffer [Tris-HCl (10 mM, pH 8)/EDTA (1 mM, pH 8)/NaCl (50 mM)]. Then, 5 ml of the same phenol solution as described above was added, and the mixture was well stirred. It was centrifuged (15,000 rpm, 15 minutes) to give about 10 ml of an upper layer. One milliliter of sodium acetate (3M, pH 6) and 10 ml isopropanol were added, and well stirred. The mixture was centrifuged (15,000 rpm, 10 minutes). The precipitates were collected, washed with 1 ml of ethanol, and dried. The precipitates were dissolved in 11.9 ml of TE buffer, and 12.6 g of cesium chloride was added. Furthermore, 0.6 ml of an ethidium bromide solution (10 mg/ml) was added. The mixture was centrifuged at 6,000 rpm for 60 hours, and fractions containing a plasmid band were extracted five times with TE buffer and isopropanol saturated with cesium chloride to remove ethidium bromide. The extract was then dialyzed against TE buffer for 24 hours in a dialyzing tube to obtain about 130 micrograms of plasmid pIJ702.

(B) Preparation of pIJ943

By substantially the same method of preparing the plasmid pIJ702 as above, plasmid pIJ943 was prepared from *Streptomyces lividans* TK24/pIJ943. About 45 micrograms of pIJ943 was obtained from 1 liter of the culture broth.

EXAMPLE 3

Isolation of Plasmid pAOY-17

Twenty micrograms of plasmid pIJ702 was dissolved in 19 microliters of TE buffer, and 10 microliters of 10×BglII buffer NaCl (1 M)/Tris-HCl (100 mM, pH 7.4)/MgCl$_2$/dithiothreitol (100 mM)/bovine serum albumin (1 mg/ml)) and 80 microliters of water were added. Five micrograms of restriction endonuclease BglII (a product of Nippon Gene; 5 to 15 units/microliter) was added, and well mixed. The mixture was incubated at 37° C. for 15 hours. The reaction product was treated with a phenol/ chloroform solution, and by using 0.1 volume of a 3 M sodium acetate solution and 3 volumes of ethanol, the digested plasmid was precipitated. The precipitates were washed with 70% ethanol and 100% ethanol. Plasmid pIJ702 digested with restriction endonuclease BglII was dissolved in TE buffer so that its final concentration became 0.1 microgram/microliter.

Three hundred micrograms of the genomic DNA of *Streptomyces thermotolerans* ATCC 11416 prepared as in Example 1 was dissolved in 900 milliliters of TE buffer, and 450 microliters of a 10 × Sau3AI buffer [NaCl (500 mM)/Tris-HCl (100 mM, pH 7.4)/MgCl$_2$ (100 mM)/dithiothreitol (10 mM) was added. Water was added to make the total volume 4.5 ml. Five units of restriction endonuclease Sau3AI were added to digest the genomic DNA partially at 37° C. for 1 hour. The restriction endonuclease Sau3AI was obtained from New England Biolabs, Tozer Road Beverly Mass., 01915-9990, U. S. A. After phenol/chloroform treatment, ethanol precipitation was carried out. The partially digested genomic DNA was dissolved in 100 microliters of TE buffer, and then electrophoresed for 15 hours at a voltage of 3 V/cm using a 0.8% agarose gel. After the electrophoresis, DNA was stained with ethidium bromide. On a transilluminator, a 5–10 kb fraction and a 10–20 kb fraction were cut out and put in a DNA cell (made by Daiichi Chemical Co., Ltd.), and DNA was electrically eluted from the gel. DNA fragments (about 50 micrograms) were obtained from the two fractions. After precipitation with ethanol, they were respectively dissolved in TE buffer to a final concentration of 0.5 microgram/microliter.

Ninety microliters (9 micrograms of DNA) of the BglII-cleaved vector-pIJ702 solution and 80 microliters (40 micrograms of DNA) and the 5–10 kb fraction of the partially digested genomic DNA were well mixed, and 150 microliters of 10 × ligation buffer Tris-HCl (500 μM, pH 8), MgCl$_2$ (100 mM), dithiothreitol (200 mM), ATP (100 mM)] and 4 microliters of T$_4$ ligase (a product of Nippon Gene; 500 units/microliter) were added, and a reaction of ligating DNA chains was carried out at 16° C. for about 15 hours. After the reaction, ethanol precipitation was carried out, and the precipitates were dissolved in 200 microliters of TE buffer.

Transformation

About $10^8$ spores of *Streptomyces lividans* were inoculated in a 250 ml Erlenmeyer flask containing a spring and 25 ml of the same YEME +34% sucrose medium as used in Example 2 (containing 5 mM of MgCl$_2$ and 0.5% of glycine but being free from thiopeptin) and cultured under shaking at 28°.C. for 32 hours. The cells were collected by centrifugal separation, washed with 10 ml of 10.3% sucrose, suspended in 4 ml of a P medium containing 1 mg/ml of lysozyme, and incubated at 30° C. for 45 minutes.

The P medium was prepared by mixing 10.3 g of sucrose, 0.025 g of K$_2$SO$_4$, 0.202 g of MgCl$_2$·6H$_2$O and 0.2 ml of a trace metal solution containing 40 mg of ZnCl$_2$, 200 mg of FeCl$_3$·6H$_2$O, 10 mg of CuCl$_2$·2H$_2$O, 10 mg of MnCl$_2$·4H$_2$O, 10 mg of Na$_2$B$_4$O$_7$·10 H$_2$O and 10 mg of (NH$_4$)$_6$Mo$_7$O$_{24}$·4H$_2$O, and adding 80 ml of deionized water to form 80 ml of a mixed solution, sterilizing the solution at 120° C. for 15 minutes, and then adding 1 ml of 0.5% KH$_2$PO$_4$, 10 ml of CaCl$_2$·2H$_2$O, and 10 ml of TES [2-(tris(hydroxymethyl(methyl)amino)methanesulfonic acid] buffer (0.25M, pH 7.2) which were separately sterilized. The mixture was incubated, and filtered through a cotton. The remaining mycelia were removed. Protoplasts were collected by centrifugation (3,000 rpm, 10 minutes) and re-suspended in a P medium in a concentration of 3 to 4×10$^7$/100 microliters. Ten microliters of the DNA solution after the ligation described above was added, and transformation was carried out in the presence of 25% PEG 1000 (a product of BDH Chemical).

The protoplasts transformed in the P medium were washed and re-suspended in 1 ml of P medium. 0.1 ml of the suspension was inoculated on a R$_2$YE agar plate, and cultured at 28° C. for 16 hours. After the culturing, a soft agar medium containing thiopeptin was superimposed so that the final concentration of thiopeptin would become 50 micrograms/ml. The R$_2$YE plate had been prepared by dissolving 10.3 g of sucrose, 0.025 g of K$_2$SO$_4$, 1.012 g of MgCl$_2$·6H$_2$O, 1 g of glucose, 0.01 g of Casamino acid (a product of Difco) and 2.2 g of bactoagar in 80 ml of distilled water, sterilizing the solution at 120° C. for 15 minutes, then adding 0.2 ml of each of the above sterilized trace metal solution, 1 ml of 0.5% KH$_2$PO$_4$, 8 ml of 3.68% CaCl$_2$·2H$_2$O, 1.5 ml of 20% L-proline, 10 ml of TES buffer (0.25M, pH 7.4), 0.5 ml of 1N NaOH and 5 ml of 10% yeast extract, putting 20 ml of the mixture in a plastic petri dish having a diameter of 9 cm, and then drying it in a clean bench for about 2 hours. On the other hand, the soft agar medium had been prepared by adding distilled water to 8 g of a nutrient broth and 3 g of bactoagar to form 1 liter of a medium, and sterilizing it at 120° C. for 15 minutes.

Isolation of Transformants Having Acylating Activity

About 2,000 transformants obtained were inoculated in an agar medium composed of 1% of glucose, 0.5% of yeast extract, 1% of malt extract, 0.02% of L-leucine, 10% of TES buffer (0.25M, pH 7.2), 1.5% of bactoagar, and 50 micrograms/ml of thiopeptin, and cultured at 28° C. for 1 week. A soft agar medium containing tylosin was overlayed so that the final concentration of tylosin would become 1000 micrograms/ml, and the culturing was continued for 24 hours. The center of each growing colony was punched out with a cork borer having a diameter of about 6 mm, and the agar piece was placed on a TLC plate (LK6DF produced by Watman Co.) and air dried. The plate was developed with a developing solvent composed of 150 ml of ethyl acetate, 3 ml of diethylamine, 1.5 ml of methanol and 3 ml of water, and acylated tylosin was detected under ultraviolet irradiation at 253.7 nm. Out of about 2,000 transformants, transformant No. Y-17 was found to produce acylated tylosin. The acylated tylosin produced by Y-17 was identified as 4″-isovaleryl tylosin from the results of analysis by TLC, HPLC, UV spectrum, NMR spectrum and antimicrobial spectrum.

Plasmid pAOY-17 was isolated from the transformant *Streptomyces lividans* #Y-17 substantially in accordance with the method described in Example 2. About 6 kb foreign DNA was seen to be inserted in this plasmid. FIG. 2 shows maps showing its restriction endonuclease cleavege sites and function. Only those restriction endonuclease sites which were significant are shown in FIG. 2, and the others were omitted.

EXAMPLE 4

Isolation of Plasmid pAO207 pIJ943 was used as a vector plasmid, and the 10-20 kb fraction described in Example 3 was used as a genome DNA digestion fragment. Substantially in accordance with the method of Example 3, the transformant *Streptomyces lividans* TK24/pAO207 having the ability to acylate tylosin was isolated. This transformant is deposited at Fermentation Research Institute, Agency of Industrial Science and Technology, Ministry of International Trade and Industry, 1-3, Higashi, 1-chome, Tsukuba-shi, Ibaraki-ken, Japan under FERM BP-1880. Plasmid pAO207 was isolated from this transformant in accordance with the method described in Example 2. Maps showing its restriction endonuclease cleavage sites and function are shown in FIG. 3. Plasmid pAO207 contained an about 13 kb DNA fragments inserted thereinto.

EXAMPLE 5

Construction of Plasmids pUY-17, pY-17ΔEco

Plasmid pAOY-17 obtained by the method described in Example 3 was digested with restriction endonuclease BglII to prepare 0.6 microgram of a digestion fragment. On the other hand, *E. coli* plasmid pUC18 (a product of Toyobo) was completely digested with restriction endonuclease BamHI, and then treated with alkaline phosphatase derived from bovine intestines (a product of Boehringer Manheim Co.) to give about 0.2 microgram of a digestion fragment. The two fragments were mixed, and 2 microliters of a 10 × ligation buffer and 1 microliter of T4-ligase were added. Water was added to adjust the total amount of the mixture to 20 microliters. The mixture was reacted at 15° C. for 16 hours. The ligated DNA was used to transform *E. coli* K-12 JM103 by the method shown below.

*E. coli* K-12 JM103 having the ability to undergo transformation used in this experiment was one produced by Pharmacia Co. A single colony was isolated from it, inoculated in 50 ml of an L-broth (prepared by adding distilled water to 10 g of bactotryptone, 10 g of sodium chloride and 5 g of bactoyeast extract to make 1 liter of a solution), and cultured at 37° C. for 5 hours. The optical density at 600 nm of the culture broth was about 0.5. The culture broth was centrifuged (3,000 rpm, 5 minutes). The cells were collected and suspended in 2 ml of 50 mM $CaCl_2$. The suspension was cooled over an ice water bath for 30 minutes and then centrifuged (3,000 rpm, 5 minutes, 4° C.) The cells were collected and re-suspended in 5 ml of 50 mM $CaCl_2$. Ten microliters of the ligated DNA was added to 100 microliters of the suspension. The mixture was incubated for 30 minutes over an ice water bath, and then given a thermal shock at 42° C. for 30 minutes. One milliliter of L-broth was added, and the mixture incubated at 37° C. for 1 hour.

The BamHI site on the plasmid pUC18 is contained in a polylinker forming part of the DNA sequence coding for the lacZα-fragment. The expression of the lacZα-fragment in *E. coli* mutant JM103 revives the beta-galactosidase activity of this *E. coli* strain. Insertion of DNA in a restriction endonuclease cleavage site of the polylinker existing in pUC18 disrupts the lacZα-fragment gene and causes a loss of the complementary ability of plasmid pUC18 with respect to JM103. β-Galactosidase hydrolyzes a colorless compound X-Gal (5-bromo-4-chloro-3-indolyl-β-D-galactopyranoside) to form a blue product, and therefore permits easy distinction between a transformant containing plasmid pUC18 and a transformant containing plasmid pUC18 having DNA inserted thereinto in the transformed cells.

The transformed strain described above is inoculated on a plate of L-agar (containing 15 g of agar per liter of L-broth) containing 100 micrograms/ml of ampicillin, 40 micrograms/ml of X-Gal and 40 micrograms/ml of IPTG (isopropyl-β-D-thiogalactopyranoside), and cultured at 37° C. for 15 hours. IPTG has the function of inducing the expression of the lac gene on plasmid pUC18.

A colony containing the plasmid having DNA inserted thereinto as was the case with plasmid pUY-17 was white. Two white colonies which showed resistance to ampicillin were separated, and the plasmids were isolated. The two colonies contained the same plasmid pUY-17. Maps showing the restriction endonuclease cleavage sites and function of plasmid pUY-17 are shown in FIG. 4.

Since plasmid pUY-17 contains a replicon of the genus Streptomyces, it can impart the ability to transform Streptomyces lividans TK24 and acylate the 4"-position of tylosin.

The plasmid pUY-17 was digested with restriction endonuclease EcoRI and then by using agarose gel electrophoresis and a DNA cell, about 9 kb fragment was obtained. About 0.1 microgram of the fragment was dissolved in 10 microliters of TE buffer, and 2 microliters of 10 × ligation buffer and 7 microliters of water were added. Furthermore, 1 microliter of T4-ligase was added. Ligation was carried out at 15° C. for 16 hours. Using the recombinant plasmid, *E. coli* K-12 JM103 was transformed.

Figure 5:
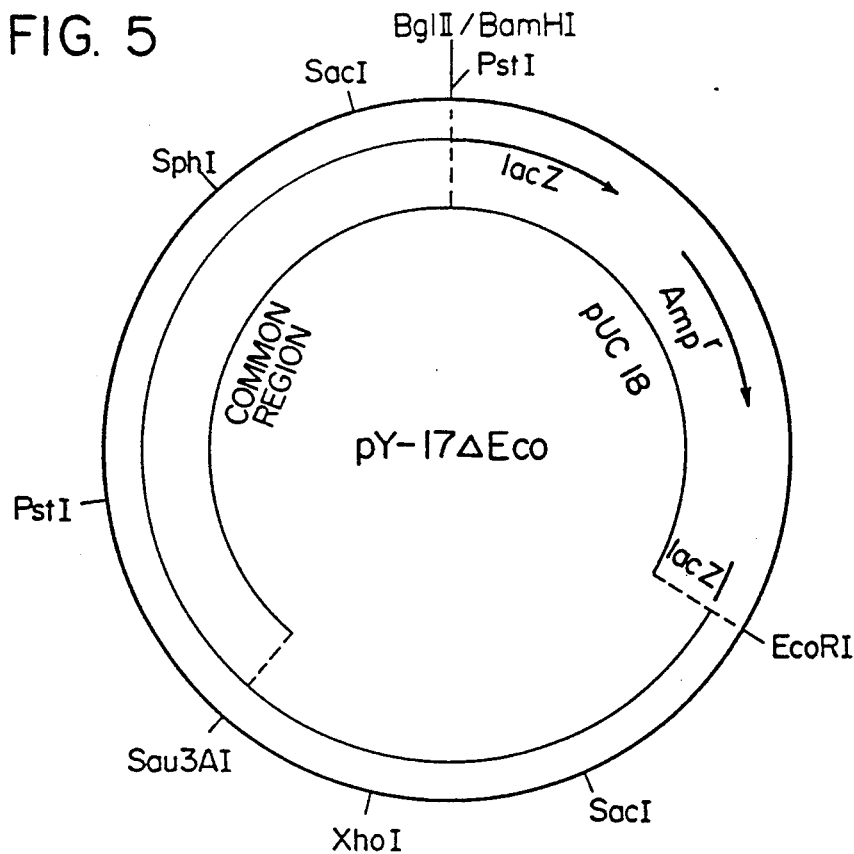
FIG. 5 is a map showing the restriction endonuclease cleavage sites and function of plasmid pY-17ΔEco.

The Plasmid pY-17ΔEco was isolated from the transformant This plasmid does not have a replicon of the genus *Streptomyces* and cannot transform *Streptomyces lividans* TK24. Maps showing the restriction endonuclease cleavage sites and function of the plasmid pY-17ΔEco are shown in FIG. 5.

EXAMPLE 6

Figure 6:
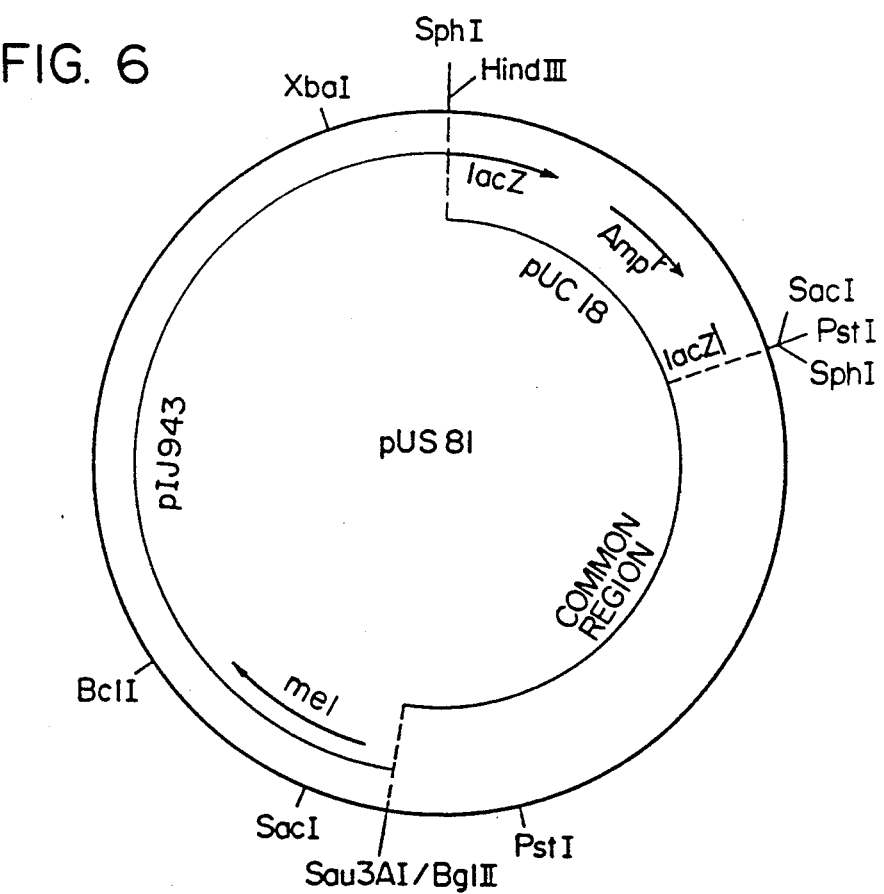
FIG. 6 is a map showing the restriction endonuclease cleavage sites and function of plasmid pUS81.

Procedure of Constructing Plasmids pUS81, pUS82, pS82ΔPst and pS82ΔSac pAO207 obtained by the method described in Example 4 was completely digested with restriction endonuclease SphI, and by using agarose gel electrophoresis and a DNA cell, about 1 microgram of a 8.8 kb DNA fragment was obtained. This fragment contained a DNA fragment which contained part of the tyrosinase gene and all of the *acy*B gene of plasmid pIJ943. This DNA fragment was ligated with the restriction endonuclease SphI digestion product of pUS18 by the method described in Example 5. *E. Coli* K-12 JM103 was transformed with the resulting recombinant plasmid, and plasmids pUS81 and pUS82 were isolated from ampicillin-resistant white transformants. FIGS. 6 and 7 give maps showing the restriction endonuclease cleavage sites and functions of plasmids pUS81 and pUS82. The direction of the inserted DNA in plasmid pUS81 was reverse to that in pUS82.

One microgram of the resulting plasmid pUS82 was digested with restriction endonuclease PstI, and agarose gel electrophoresis and a DNA cell, about 0.1 microgram of a 5.2 kb fragment was obtained. This fragment was dissolved in TE buffer, and ligated by using a $T_4$ ligase. Then, by using the recombinant plasmid, E. coli K-12 JM103 was transformed by the method described in Example 5. About 20 colonies which were white and ampicillin-resistant were separated. Plasmids were isolated from these transformants. All plasmids obtained were pS82ΔPst. FIG. 8-(a) shows a map of the restriction endonuclease cleavage sites and function of plasmid pS82ΔPst. Part of the acyB gene in the plasmid pS82ΔPst was deleted.

By the same method, plasmid pUS82 was digested with restriction endonuclease SacI and self-ligated to obtain plasmid pS82ΔSac. FIG. 9 gives a map showing the restriction endonuclease cleavage sites and function of plasmid pS8ΔSac. Plasmid pS82ΔSac completely retained the acyB gene.

EXAMPLE 7

Restriction of the acyB Gene

Plasmids pAOY-17 and pAO207 were prepared by the methods described in Examples 3 and 4 in order to restrict the acyB gene contained in the DNA fragments inserted into the plasmids pAOY-17 and pAO207. A detailed examination of the inserted DNA portions of the two plasmids showed that they have a DNA fragment having a size of about 4 kb in common (see FIGS. 2 and 3). Plasmids pS82ΔPst and pS82ΔSac having this common DNA region were prepared by the method described in Example 6.

Plasmid pS82ΔSac (0.5 microgram) was dissolved in 10 microliters of TE buffer, and 2 microliters of 10 × SphI buffer and 10 units of restriction endonuclease SphI were added. Water was added to make the total amount 20 microliters. The plasmid was digested at 37° C. for 4 hours. Two microliters of the reaction mixture was subjected to agarose gel electrophoresis, and it was determined that the digestion came to completion.

Separately, 0.5 microgram of plasmid pIJ702 prepared by the method described in Example 2 was digested in the same way as above, treated with alkaline phosphatase derived from bovine intestines at 37° C. for 30 minutes, and then heated at 70° C. for 15 minutes. 0.1 microgram of the SphI digested product of plasmid pS82ΔSac described above was added, and the mixture was subjected to phenol/chloroform treatment and precipitation with ethanol. The DNA pellets obtained by ethanol precipitation were dissolved in 10 microliters of TE buffer, and ligated by the method described in Example 3. Streptomyces lividans TK24 was transformed with the reaction product, and the ability of the resulting transformants to acylate the 4"-position of tylosin was examined. All the transformants acylated the 4"-position of tylosin.

In quite the same way as in the case of plasmid pS82ΔSac, plasmid pS82ΔPst was inserted into the SphI site of plasmid pIJ702, and Streptomyces lividans TK24 was transformed with the resulting recombinant plasmid. None of the transformants showed the ability to acylate the 4"-position of tylosin.

From the results obtained, it seems that in the map shown in FIG. 9, a region ranging from Sau3AI/BglII to PstI is essential for imparting the ability to acylate the 4"-position of tylosin, and considered as part of the acyB gene.

Plasmid pUS81 was prepared by the method described in Example 6. One microgram of it was dissolved in 10 microliters of TE buffer, and 2 microliters of 10 × SacI buffer and 10 units of a restriction endonuclease were added. Water was then added to make 20 microliters. The reaction solution was placed on 8% agarose gel, and electrophoresed. An agarose containing an about 3.3 kb DNA fragment was cut out and electrically eluted by using a DNA cell thereby to give about 0.1 microgram of a DNA fragment. This DNA fragment contained part (240 bases) of the tyrosinase gene of plasmid pIJ943 and part of the multicloning sites of plasmid pUC18.

The resulting DNA fragment having a size of about 3.3 kb was inserted into the SacI site of plasmid pIJ702 according to the method of Example 3, and Streptomyces lividans TK24 was transformed with the resulting recombinant plasmid. All transformants acylated the 4"-position of tylosin. The plasmids held by the transformants were slightly unstable.

The restriction endonuclease cleavage sites of the DNA fragment containing the acyB gene restricted to about 3.1 kb were determined (see FIG. 1). In preparing the restriction endonuclease map shown in FIG. 1, the DNA fragment was digested with various restriction endonucleases either singly or in combination. The digested products were subjected to agarose gel electrophoresis and the migration distance of each of the DNA fragments was measured and its size was determined. The agarose gel concentration was varied between 0.6% and 1% according to the size of the DNA fragment. λ/HindIII and φ×174/HaeIII (both produced by Nippon Gene) were used as size markers for DNA.

EXAMPLE 8

Determination of the DNA Base Sequence of the Enzyme Gene acyB Acylating a Macrolide Antibiotic A PstI-SacI fragment (1.2 kb) of the acyB gene and its PstI-SphI fragment (2.1 kb) were subcloned into E. coli vector pUC18 to obtain plasmid pMAB7 [FIG. 8-(b)] and plasmid pS82ΔPst (see Example 6) containing these fragments respectively were obtained. These two plasmids or new plasmids obtained by deleting a specified region from them were used for determination of DNA base sequence. To cause deletion, a method was used in which deletion took place between a suitable cloning site of the vector and a suitable restriction site of the acyB fragment For example, a deleted plasmid was constructed by the following method in order to obtain a plasmid convenient for determining the sequence from the NcoI site of pS82ΔPst.

PS82ΔPst (5 micrograms)
| NcoI, 10 units (Nippon Gene), digested
| at 37° C. for 5 hours.
| HindIII, 10 units (Nippon Gene)
↓

-continued

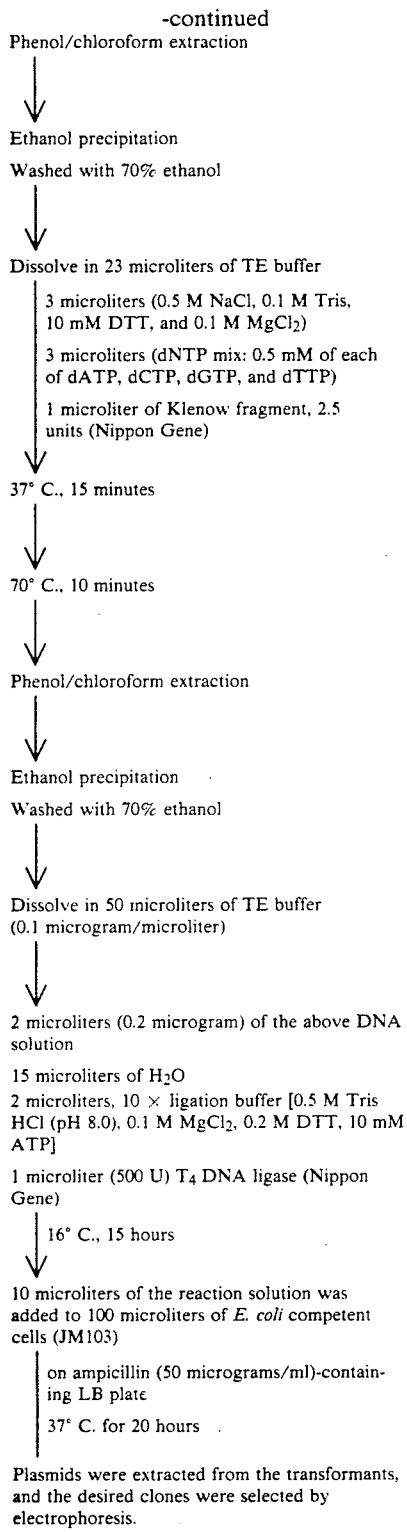

As another deleting method, the DNA fragment was gradually decomposed from the specific terminal by exonuclease III and S1 nuclease in a time-dependent manner. Thus, a series of continuous deletion plasmids having an overlapping region convenient for sequence determination were obtained. For example, a series of deletion plasmids obtained by digesting from the ApaI site of pMAB7 were obtained by the following procedure.

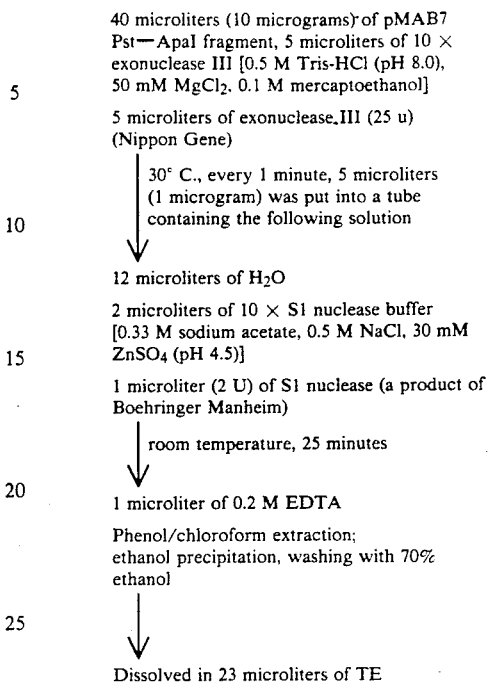

Subsequently, the same procedure as in the above method beginning with the reaction with the Klenow fragment was carried out.

The two plasmids obtained by subcloning and deletion plasmids derived therefrom were modified with alkali to form single-stranded DNA. For one reaction, 1 to 2 micrograms of modified DNA was used as a template DNA for sequencing. The sequencing was in accordance with the method of Hattori et al. [Hattori, M. & Sasaki, Y: Anal. Biochem. 152, 232-328 (1986)]. The method of sequencing was basically in accordance with the Spanger's dideoxy chain termination method [Sanger, F. et al.: Proceedings of the National Academy of Sciences, U. S. A., 74, 5463-5467 (1977)). Specifically, the DNA base sequence containing a region coding for the acyB gene was determined by using a sequence kit (made by United States Biochemical Corporation) and [$\alpha$-$^{32}$P] dCTP (a product of Amersham). The DNA base sequence determined is shown in FIG. 10 of the accompanying drawings. The determined DNA base sequence was examined for reading frames. Specifically, the base sequence was examined in accordance with the report of M. J. Bibb et al. [M. J. Bibb et al.; "Gene", vol. 30, pages 157-166 (1984)], and an open reading frame leading from the central part of the sequence towards the Sau3AI terminal and an open reading frame leading toward the SphI terminal were found. These two open reading frames were named acyB1 and acyB2. The acyB1 begins with the 1245th ATG and ends with the 81st TAG in FIG. 10, whereas the acyB2 begins with the 1569th GTG or 1608th ATG and ends with the 2730th TGA. FIG. 11-(a) and FIG. 11-(b) respectively show the DNA base sequences and amino acid sequence of acyB1 and AcyB2.

EXAMPLE 9

Productivity of 4"-acylated tylosin using a microorganism transformed with a plasmid containing DNA fragment having the acyB gene of the invention:

*Streptomyces lividans* TK24 was transformed with plasmid pAO207 by the method of Example 3. The transformants were cultured by the following procedure. The transformants were inoculated in a GYM agar slant medium containing 50 micrograms/ml of thiopeptin (0.4% of glucose, 0.4% of yeast extract, 1% of malt extract and 1.5% of agar; adjusted to pH 6.8). One loopful of the grown transformants was inoculated in 25 ml of a seed culture medium (2% of soluble starch, 2% of soybean meal, 0.1% of yeast extract, 0.1% $K_2HPO_4$, 0.05% $MgSO_4\cdot 7H_2O$ and 5 micrograms/ml of thiopeptin), and cultured at 28° C. for 48 hours under shaking.

One milliliter of the prepared seed culture was inoculated in 50 ml of a production medium containing 30 micrograms/ml of thiopeptin (4% of galactose, 2% of soybean meal, 0.1% of yeast extract, 0.05% of $KH_2PO_4$ and 0.05% of $MgSO_4\cdot 7H_2O$), and cultured at 28° C. for 48 hours. A mixed solution of tylosin and L-leucine was added so that their final concentrations would be 1,000 micrograms/ml and 400 micrograms/ml, and the culturing was continued at 28° C. for 48 hours. After the culturing, the fermentation broth was adjusted to pH 9.0 with 0.1M Na , and the broth was extracted with an equal amount of toluene. Twenty microliters of the toluene layer was spotted on a silica gel TLC plate Art 5715 made by Merck Co.], and developed with a solvent composed of 150 ml of ethyl acetate, 3 ml of diethylamine, 1.5 ml of methanol and 3 ml of water. The solvent was removed by air drying. The amount of the acylated tylosin produced was measured by a TLC-chromatoscanner CS-920 (made by Shimadzu Seisakusho). The results are shown in Table 1.

TABLE 1

| Microorganism strain | Plamid contained | Amount(*) of 4"-isovaleryl tylosin produced |
|---|---|---|
| *S. lividans* TK24 | None | 0 |
| " | pIJ943 | 0 |
| " | pAO207 | 1.25 |
| *S. thermotolerans* ATCC 11416 | None | 1 |

(*)The amount relative to that produced by *S. thermotolerans* ATCC 11416. The strain containing no plasmid was cultured by using a seed culture medium and production medium which did not contain thiopeptin.

(*) The amount relative to that produced by *S. thermotolerans* ATCC 11416. The strain containing no plasmid was cultured by using a seed culture medium and production medium which did not contain thiopeptin.

EXAMPLE 10

Specific activity of an enzyme capable of acylating the 4"-position of tylosin in the case of using a microorganism transformed with a plasmid containing a DNA fragment containing the *acy*B gene of the invention:

In accordance with the methods described in Examples 1 and 4 *Streptomyces lividans* TK24 containing plasmid pAO207 and *Streptomyces thermotolerans* ATCC 11416 containing plasmid pAO207 were cultured. About 10 g of the cells were suspended in 20 ml of TES buffer (0.25M, pH 7.2). The suspension was treated at 80 KW for 5 minutes in an ice water bath by using an ultrasonic disrupter (model UR 200-P made by Tomy Seiko Co., Ltd.). It was centrifuged (14,000 rpm, 30 minutes), and the activity of an enzyme in the supernatant which was capable of acylating the 4"-position of tylosin was measured. The amount of proteins in the supernatant was measured by UV absorption at 280 nm (calculated by taking $E_{1\,cm}^{1\%} = 10.0$) The conditions for measuring the enzyme activity were as follows:

Crude enzyme solution: 50 microliter
TES buffer (0.25M, pH 7.2): 130 microliters
Tylosin (10 mM): 10 microliters
Isovaleryl CoA (10 mM): 10 microliters
Incubated at 30° C. for 1 hour After the reaction, 20 microliters of 1N-NaOH was added, and the solution was extracted with 50 microliters of toluene. Twenty microliters of the toluene extract was spotted on a silica gel TLC plate, and the amount of acylated tylosin formed was measured by the method described in Example 8. The results are shown in Table 2.

TABLE 2

| Microorganism strain | Plasmid contained | Specific activity of the enzyme capable of acylating the 4"-position of tylosin |
|---|---|---|
| *S. lividans* TK24 | None | 0 |
| " | pIJ943 | 0 |
| " | pAO207 | 1.5 |
| *S. thermotolerans* ATCC 11416 | None | 1 |

The specfic activity was calculated as units/mg protein, and the relative value with respect to *S. thermotolerans* ATCC 11416 is shown in the table. One unit is defined as nmoles of acylated tylosin/hour.

EXAMPLE 11

Production of 4"-acylated tylosin using a microorganism transformed with a plasmid containing a DNA fragment containing the *acy*B gene of the invention:

(A) Preparation of pIJ350

Two micrograms of DNA of plasmid pIJ702 was dissolved in 50 microliters of Bcl buffer 10 mM of Tris-HCl (pH 7.5), 7 mM of $MgCl_2$, 60 mM of NaCl and 7 mM of 2-mercaptoethanol. Two units of restriction endonuclease BclI (a product of Toyobo) was added to diest the DNA partially at 50° C. for 5 minutes. The digestion product was treated with ethanol/chloroform, and precipitated with ethanol. The purified DNA was dissolved in 50 microliters of a ligation buffer, and 2 microliters of $T_4$ ligase (a product of Nippon Gene; 500 units/microliter) was added. The ligation reaction was carried out at 16° C. for 15 hours. After the reaction, the reaction mixture was precipitated with ethanol, and then dissolved in 100 microliters of TE buffer.

Protoplasts of *Streptomyces lividans* TK24 were prepared by the same method as in Example 3, and transformed with the partially BclI digested product of pIJ702 by the same method as in Example 3. Colonies which had resistance to thiopeptin (50 micrograms/ml) and did not produce melanin pigment were selected, and the plasmid was extracted and purified to give pIJ350 (4.1 kb).

(B) Construction of pMAB1

*E. coli* plasmid pUC18 was linked to plasmid pIJ350 of *Actinomycetes*, and multicloning sites were introduced into pIJ350.

pIJ350 was dissolved in 50 microliters of PstI buffer 20 mM of Tris-HCl (pH 7.5), 10 mM of $MgCl_2$ and 150 mM of NaCl], and 1 microliter of restriction endonuclease PstI (a product of Nippon Gene; 20,000 units/ml) was added. The mixture was reacted at 37° C. for 4 hours. The reaction mixture was precipitated with ethanol, and dissolved in 50 microliters of distilled water. Separately, 2 micrograms of plasmid (pUC-Bg) resulting from changing the HincII (SalI) site of pUC18 to a BglII site was dissolved in 50 micrograms of Pst buffer, and digested with 20 units of restriction endonuclease PstI at 37° C. for 4 hours. The digestion product was purified by ethanol precipitation, and dissolved in 50 microliters of distilled water. The two DNA solutions were mixed, and 10 microliters (10-fold concentration) of a ligase buffer and 1,000 units of $T_4$ ligase were added, and the reaction was carried out at 16° C. for 20 hours. The DNA was purified by ethanol precipitation treatment, and finally the precipitate was dissolved in 50 microliters of TE buffer. By using 10 microliters of the solution, $E$ $coli$ K-12 JM103 was transformed. The plasmids in transformants which were ampicillin-resistant and white on an X-gal plate under IPTG inducing conditions were examined. There was obtained plasmid pUJ350 (6.8 kb) in which the PstI-digested fragment of plasmid pIJ350 was linked to the PstI site of plasmid pUC-Bg.

Fifteen micrograms of DNA of the plasmid pUS81 shown in Example 6 was dissolved in 50 microliters of SacI buffer 10 mM of Tris-Hcl (pH 7.5), 7 mM of $MgCl_2$, 20 mM of 2-mercaptoethanol, and 100 micrograms/ml of bovine serum albumin), and 2.5 microliters of restriction endonuclease SacI (a product of Nippon Gene, 15 units/ml) was added to digest the DNA at 37° C. for 4 hours. The reaction solution was subjected to 0.8% agarose electrophoresis, and agarose containing a DNA fragment having a size of about 3.3 kb was cut out. The agarose gel was put in a DNA cell (made by Daiichi Chemical Co.) and the DNA was eluted and recovered by electrophoresis. It was precipitated with ethanol and then dissolved in 50 microliters of TE buffer. Twenty microliters of this solution was mixed with 2 micrograms of the SacI-digested DNA fragment of pUJ350, and 10 microliters of a ligation buffer (10-fold concentration), 4 microliters of $T_4$ ligase (a product of Nippon Gene; 500 units/microliter) and 70 microliters of distilled water were added, and the reaction was carried out at 16° C. for 15 hours. After the reaction, precipitation with ethanol was carried out, and the precipitate was dissolved in 100 microliters of TE buffer. $E.$ $coli$ K-12 JM103 was transformed by using 20 microliters of the resulting DNA solution by the method described in Example 5. Plasmids contained in ampicillin (50 micrograms/ml)-resistant colonies were examined. Plasmid pMAB1 in which a DNA fragment containing the acyB gene was inserted into the SacI site of pUJ350 was obtained. The foregoing plasmid constructing process is shown in FIG. 12.

Introduction of pMAB1 into $S.$ $lividans$ and Conversion of a Macrolide $S.$ $lividans$ TK24 was transformed with plasmid pMAB1 by the method of Example 3. The transformants were inoculated in a GYM agar slant medium containing 50 micrograms/ml of thiopeptin (0.4% of glucose, 0.4% of yeast extract, 1% of malt extract, and 1.5% of agar; adjusted to pH 6.8). One loopful of the grown transformants was inoculated in 25 ml of a seed culture medium (2% of soluble starch, 2% of soybean meal, 0.1% of yeast extract, 0.1% of $K_2HPO_4$, 0.05% of $MgSO_4 \cdot 7H_2O$ and 5 micrograms/ml of thiopeptin), and cultured with shaking at 28° C. for 48 hours. One milliliter of the seed culture prepared was inoculated in a production medium containing 30 micrograms/ml of thiopeptin (4% of galactose, 2% of soybean meal, 0.1% of yeast extract, 0.05% of KH and 0.05% of $MgSO_4 \cdot 7H_2O$) and cultured at 28° C. for 48 hours. To the culture broth was added tylosin, spiramycin, angoramycin, leucomycin U, leucomycin V or deltamycin X as a macrolide having —OH group at the 4″-position so that its concentration became 200 micrograms/ml. Furthermore, L-leucine was added so that its concentration became 200 micrograms/ml. The culturing was continued at 28° C. for 48 hours. After the culturiing, the pH of the culture broth was adjusted to 9.0 with 0.1M $Na_3PO_4$ and it was extracted with an equivalent weight of toluene. Twenty microliters of the toluene layer was spotted on a silica gel thin layer plate (Art 5715 made by Merck and Co.) and a developing solvent of the following composition.

(1) 30 ml of n-hexane, 10 ml of acetone, 8 ml of methanol, 25 ml of benzene and 20 ml of ethyl acetate;

(2) 85 ml of benzene, 10 ml of methanol and 5 ml of toluene;

or (3) 50 ml of benzene and 50 ml of acetone.

After the development, the solvent was removed by air drying. The residue was analyzed by a TLC chromatoscanner (CS-930 of Shimadzu Seisakusho). The mobilities (Rf) of 4″-OH macrolides and 4″-O-isovaleryl macrolides are shown in the parentheses.

Tylosin (0.22), 4″-O-isovaleryl tylosin (0.49); spiramycin I (0.057), 4″-O-isovaleryl spiramycin I (0.25); angoramycin (0.26), 4″-O-isovaleryl angoramycin (0.51)

The foregoing were obtained by using the developing solvent (1).

Leucomycin U (0.12), 4″-isovaleryl leucomycin U (0 65); leucomycin V (0.08), 4″-isovaleryl leucomycin V (0.50).

The foregoing were obtained by using the developing solvent (2).

Deltamycin X (0.20), 4″-isovaleryl deltamycin X (0.70).

The foregoing were obtained by using the developing solvent (3).

(D) Transformation with pMAB1

One loopful of a slant culture of $Streptomyces$ $fradiae$ was inoculated in a 250 ml Erlenmeyer flask holding GPY medium (1.0% of glucose, 0.4% of polypeptone, 0.4% of yeast extract, 0.05% of $MgSO_4 \cdot 7H_2O$, 0.1% of $K_2HPO_4$ and 0.05% of glycine, pH 7.2), and cultured with shaking at 28° C. for 48 hours. 0.5 ml of the culture broth was inoculated in a 250 ml Erlenmeyer flask containing a spring and holding 25 ml of a YEME +15% sucrose medium (containing 5 mM of $MgCl_2$ and 0.5% of glycine) and culture with shaking a 28° C. for 40 hours. The cells were collected by centrifugation (3,000 rpm, 15 minutes) washed with 10 ml of 10.3% sucrose, suspended in 4 ml of P medium containing 1 mg/ml of lysozyme, and reacted at 30° C. for 1 hour. The composition of the P medium was as shown in Example 3. After the reaction, the reaction mixture was filtered through cotton, and the remaining mycelia were removed. Protoplasts were collected by centrifugation (3,000 rpm, 10 minutes) and suspended in P medium so that their concentration became $3 \times 10^9/100$ microliters. The resulting protoplasts were transformed with 10 microliters liters in the presence of 25% PEG 1000 (a product of BDH Chemical). The transformed protoplasts were washed with the P medium, and re-suspended in 1 ml of the P medium. One milliliter of the suspension was inoculated in an R3 medium [13.5 g of sucrose, 0.05% of KCl, 1.0 g of glucose, 0.4 g of polypeptone, 0.4 g of yeast extract, 0.573 g of TES buffer, 6.1 ml of 10% $MgCl_2$, 2.0 g of bactoagar and 100 ml of distilled water; after autoclave sterilization, 1.0 ml of $KH_2PO_4$ (0.5%), 0.3 ml of $CaCl_2$ (5M) and 1.8 ml of NaOH (1N) were added), and cultured at 28° C. for 16 hours. After the culturing, a soft agar medium containing thiopeptin was overlayed so that the final concentration of thiopeptin would become 5 micrograms/ml or 25 micrograms/ml. The culturing was further carried out at 28° C. for 7 days. The soft agar medium had been prepared by adding 1 liter of distilled water to 8 g of a nutrient broth and 3 g of bactoagar and sterilizing the mixture at 120° C. for 15 minutes in an autoclave.

Many colonies appeared on the medium containing 5 micrograms/ml of thiopeptin. One colony which showed resistance to 25 micrograms/ml of thiopeptin was named Streptomyces fradiae MAB-01 (to be referred to as MAB-01), and a production test was carried out.

One loopful of MAB-01 was inoculated in a 250 ml Erlenmeyer flask containing a coil and holding a production medium (0.5% of soluble starch, 0.5% of glucose, 0.5% of yeast extract, 1.0% of malt extract and 5 micrograms/ml of thiopeptin), and cultured with shaking at 28° C. for 21 days. Then, 1 ml of the culture broth was taken, and 0.2 g of $K_2HPO_4$ and 0.2 ml of toluene were added. The mixture was vigorously stirred to extract the culture broth with toluene. The upper toluene layer was separated by centrifugation (3,000 rpm, 10 minutes), and subjected to thin-layer chromatography. Merck Art 5715 was used as a thin-layer plate, and a mixture of 75 ml of ethyl acetate, 1.5 ml of diethylamine, 1.5 ml of water and 0.75 ml of methanol was used as a developing solvent. The plate was dried and analyzed at a wavelength of 280 nm by a chromatoscanner (CR-930 of Shimadzu seisakusho). After immersion in 10% $H_2SO_4$, the plate was heated at 105° C. for 5 minutes to color it, and the position of the macrolides produced was determined. The Rf (relative mobility) of tylosin was 0.62, and in addition to tylosin, 4"-acetyl tylosin (Rf=0.69), 4"-propionyl tylosin (Rf=0.74) and 4"-isovaleryl tylosin (Rf=0.77) were noted as the products of transformants.

The corresponding microorganism not transformed with plasmid pMAB1 was not seen to produce acylated tylosin.

(E) Identification of 4"-Isovaleryl Tylosin

The culture fluid from 1 liter of the above production medium (50 ml × 20) was extracted with ethyl acetate at a pH of 8.5. The extract was extracted with 200 ml of acidic water (0.01N-HCl), and again adjusted to pH 8.5, and back extracted with 50 ml of ethyl acetate. The extract was concentrated to 10 ml, and spotted in a band form to five thin-layer plates (Art 5715 produced by Merck & Co.) at a rate of 2 ml, followed by developing with the aforesaid developing solvent. After air drying, silica gel at a spot portion having an Rf value of 0.77 was scraped off and extracted with 10 ml of acetone. The extract was evaporated to dryness in a vacuum evaporator-concentrator to give 4 mg of of a white powder which had the following physical and chemical properties.

Molecular weight: 999 (a dehydration ion peak 982 was obtained by a chemical impact mass spectrometer analysis)

Specific optical rotation $[\alpha]_D^{24}$ (c1.0, MeOH): −50.8

Ultraviolet absorption peak $\lambda_{max}^{EtOH}(E_1\ _{cm}^{1\%})$: 282 (217)

$^1$H—NMR (δ, ppm): 0.97 [$OCCH_2CH(CH_3)_2$], 1.8 (12—$CH_3$), 2.28 [$OCCH_2CH(CH_3)_2$], 2.5 [$N(CH_3)_2$], 3.5 (3"—$OCH_3$), 3.6 (2'''—$OCH_3$), 4.15 (H1'), 4.55 (H1'''), 4.60 (H4"), 5.05 (H1"), 5.95 (H13), 6.25 (H10), 7.3 (H11), 9.7 (CHO).

FIG. 13 shows the $^1$H—NMR chart. By comparing the above results with the literature values [R. Okamoto et al.: The Journal of Antibiotics, vol. 33, pages 1300-1308 (1980)], the above spotted portion was determined to be 4"-O-isovaleryl tylosin.

Silica gel of a spot portion having an Rf of 0.69 was scraped off, and subjected to acetone extraction, concentration and drying by the same method as above to give 4.5 mg of a white powder. Its physical and chemical properties were examined.

Molecular-weight: 957

Specific optical rotation $[\alpha]_D^{24}$ (c1.0, MeOH): −50.5

Ultraviolet absorption peak $\lambda_{max}^{EtOH}(E_1\ _{cm}^{1\%})$: 283 (218)

$^1$H—NMR (δ, ppm): 1.8 (12—$CH_3$), 2.13 (—$COCH_3$), 2.5 [$N(CH_3)_2$], 3.5 (3"—$OCH_3$), 3.63 (2'''—$OCH_3$), 4.2 (H1'), 4.52 (H1'''), 4.57 (H4"), 5.05 (H1"), 5.9 (H13), 6.23 (H10), 7.3 (H11), 9.7 (CHO).

FIG. 14 shows the $^1$H-NMR chart.

The results led t the identification of the above substance was 4"-O-acetyl tylosin.

We claim:

1. A purified and isolated DNA fragment derived from Streptomyces thermotolerans, having a size of about 3.1 kb and bounded by the Sau3AI and SphI restriction endonuclease sites depicted in FIG. 1, said fragment comprising DNA sequences coding for an acyB1 gene and acyB2 gene.

2. A purified and isolated DNA fragment consisting essentially of a DNA sequence the acyB2 gene product according to the following amino acid sequence

| Met | His | Ser | Ile | Pro | Cys |
|-----|-----|-----|-----|-----|-----|
| Gly | Ser | Lys | Pro | Ser | Ala |
| Ser | Met | Trp | Asp | Thr | Gly |
| Val | His | Asp | Asp | Phe | Asp |
| Thr | His | Ile | Ser | Glu | Thr |
| Cyc | Ser | Glu | Leu | Phe | Ser |
| Ser | Leu | Arg | Arg | Ala | Asp |
| Gln | Arg | Lys | Arg | Gly | Glu |
| Gln | Tyr | Val | Arg | Gly | Leu |
| Leu | Thr | Ala | Gln | Gly | Arg |
| Lys | Thr | Ala | Arg | Asn | Leu |
| Ala | Ala | Phe | Val | Gly | Glu |
| Gly | Ala | Ala | Asp | Gln | Asn |
| Leu | His | His | Phe | Val | Ala |
| Gly | Ser | Thr | Trp | Asp | Trp |
| Arg | Ser | Val | Arg | Ala | Ala |
| Leu | Ala | Arg | Tyr | Ala | Asp |
| Gln | Thr | Val | Arg | Gly | Asp |
| Ala | Trp | Val | Ile | Arg | Pro |
| Met | Val | Val | Tyr | Lys | Ala |
| Gly | Gly | Arg | Ser | Val | Gly |
| Val | Gly | Arg | Arg | Phe | Val |
| Pro | Asp | Leu | Gly | Arg | Val |
| Val | Ser | Cys | Gln | Gln | Ser |
| Tyr | Gly | Leu | Trp | Leu | Ala |
| Ser | Asp | Ala | Met | Ser | Ala |
| Pro | Val | Asn | Trp | His | Leu |
| Thr | Leu | Gly | Gly | Gly | Pro |
| Gly | Asp | Arg | His | Asp | Arg |
| Gln | Leu | Ser | Ala | Tyr | Gly |

| | | | | | |
|---|---|---|---|---|---|
| Glu | Glu | Glu | Lys | Leu | Val |
| Asp | Leu | Val | Ala | Glu | Leu |
| Thr | Arg | Ser | Asn | Arg | Val |
| Leu | Ala | Arg | Pro | Val | Val |
| Met | Asp | Ala | Arg | Ile | Ala |
| Thr | Leu | Pro | Arg | Leu | Val |
| Arg | Ala | Leu | Ser | Ala | Ala |
| Asp | Gln | Ser | Phe | Leu | Leu |
| Arg | Val | Ser | Gly | Asp | Leu |
| Pro | Leu | Ala | Leu | Ala | Gly |
| Ser | Arg | Gly | Gln | Leu | Asp |
| Arg | Arg | Ala | Gln | Val | Trp |
| Pro | Ala | Gln | His | Leu | Met |
| Glu | Gln | Leu | Lys | Arg | Leu |
| Arg | Arg | Pro | Val | Glu | Trp |
| Gln | Gly | Ser | Ile | Ser | Phe |
| Val | Ala | Pro | Cys | Asn | Val |
| Val | Leu | Thr | Asp | Gln | Leu |
| Pro | Gln | Arg | Thr | Leu | Leu |
| Leu | Phe | Gly | Val | Trp | Arg |
| Ala | Asn | Arg | Arg | Arg | Pro |
| Ala | Asp | Leu | Trp | Lue | Thr |
| Asp | Lue | Thr | Ser | Trp | Asn |
| Arg | Gly | Ala | Leu | Leu | Arg |
| Leu | Ala | Met | Leu | Thr | Cys |
| Arg | Val | Asp | Ala | Asp | Phe |
| Ala | Arg | Val | Ser | Leu | Gly |
| Val | Gly | Ile | Arg | Asp | Phe |
| Glu | Gly | Arg | Ser | Phe | Gln |
| Gly | Trp | His | Arg | His | Val |
| Thr | Leu | Ala | Ser | Ile | Ala |
| His | Ala | Leu | Arg | Leu | Ser |
| Cys | Thr | Asp | Thr | Ala | Arg |
| Thr | Pro | Thr | Ala | Pro | Ala |
| Leu | Ser | Arg. | | | |

3. A purified and isolated DNA fragment consisting essentially of a DNA sequence encoding the acyB2 gene product according to the following base sequence

```
      1569
        GT GCACAGTATT
                    1600
CCGTGTGGCT CAAAACCGTC
GGCCTCCATG TGGGACACCG
GTGTCCATGA CGACTTCGAT
ACGCACATCT CCGAGACCTG
CTCGGAGCTG TTCAGTTCGC
                    1700
TGCGCCGGGC CGACCAGCGC
AAGAGGGGCG AACAGTACGT
CCGTGGTCTG CTCACCGCTC
AGGGACGCAA GACCGCCCGC
AACCTCGCCG CGTTCGTCGG
                    1800
TGAAGGCGCC GCGGACCAGA
ACCTCCACCA CTTCGTGGCC
GGATCCACCT GGGACTGGCG
CTCCGTGCGT GCCGCGCTGG
CCCGCTACGC CGACCAGACG
                    1900
GTACGCGGGG ACGCGTGGGT
GATCCGCCCC ATGGTGGTCT
ACAAGGCAGG GGGACGGTCG
GTCGGCGTGG GCCGGCGCTT
CGTACCCGAC CTGGGGCGGG
                    2000
TGGTCAGCTG TCAGCAGAGC
TACGGGCTCT GGCTCGCCTC
CGACGCCATG TCGGCACCGG
TGAACTGGCA TCTGACGCTG
GGCGGCGGAC CGGGCGACCG
                    2100
TCACGATCGG CAGCTGAGCG
CGTACGGCGA GGAGGAGAAG
CTCGTCGACC TGGTGGCGGA
ACTCACGCGC TCGAACCGGG
TGTTGGCGCG TCCGGTGGTG
                    2200
ATGGACGCGC GGATCGCCAC
GCTGCCCCGG CTGGTTCGGG
CGCTGTCCGC GGCTGATCAA
TCGTTTCTCT TAAGGGTGAG
CGGCGATCTT CCGCTCGCCC
                    2300
TCGCCGGCAG CCGGGGCCAA
CTGGACAGGC GCGCGCAGGT
CTGGCCCGCC CAGCACCTCA
TGGAACAGCT CAAGCGGCTC
AGGCGCCCTG TGGAGTGGCA
                    2400
GGGCTCCATC AGCTTCGTCG
CCCCGTGCAA CGTGGTGCTG
ACCGATCAGC TGCCGCAGCG
CACGCTCCTG CTGTTCGGGG
TGTGGCGCGC CAACCGCAGG
                    2500
CGACCCGCGG ACCTGTGGCT
CACCGACCTC ACGTCCTGGA
ACCGCGGCGC ACTGCTGCGG
CTGGCCATGC TGACCTGCCG
CGTGGACGCC GACTTCGCCG
                    2600
GCGTCAGCCT GGGCGTCGGC
ATCCGCGACT TCGAGGGCCG
CTCCTTCCAG GGCTGGCACC
GTCACGTGAC ACTGGCCTCG
ATAGCCCACG CCCTACGCCT
                    2700
TTCCTGCACC GACACCGCCC
GCACCCCCAC GGCCCCGGCC
        2730
CTGTCCCGCT GA
```

4. The DNA fragment and the DNA restriction fragment according to claim 1 in which the microorganism of the genus Streptomyces is Streptomyces thermotolerans ATCC 11416.

5. The DNA fragment and the DNA restriction fragment according to claim 1 which contains a DNA portion coding for the following amino acid sequence

| | | | | | |
|---|---|---|---|---|---|
| Met | Pro | Leu | Pro | Lys | His |
| Leu | Pro | Ala | Leu | Gly | Gly |
| Met | Arg | Phe | Ile | Ser | Ala |
| Leu | Leu | Val | Phe | Thr | Ser |
| His | Ile | Ser | Thr | Gln | Pro |
| Phe | Phe | Lys | Asn | Thr | Glu |
| Ile | Asn | Ser | Ala | Leu | Gln |
| Phe | Pro | Leu | Asn | Arg | Leu |
| Gly | Pro | Leu | Thr | Val | Ser |
| Phe | Phe | Phe | Met | Leu | Ser |
| Gly | Phe | Val | Leu | Thr | Trp |
| Ala | Gly | Leu | Pro | Asp | Lys |
| Ser | Lys | Val | Asn | Phe | Trp |
| Arg | Arg | Arg | Thr | Val | Arg |
| Ala | Tyr | Ser | Leu | His | Leu |
| Pro | Val | Leu | Leu | Val | Thr |
| Leu | Leu | Ile | Val | Leu | Ala |
| Leu | Asn | Glu | Pro | Ans | Met |
| Gly | Arg | Ser | Vla | Trp | Asp |
| Gly | Leu | Leu | Thr | Asn | Leu |
| Leu | Leu | Ile | Gln | Ala | Trp |
| Phe | Pro | Asp | His | His | Glu |
| Tyr | Gly | Ser | Met | Asn | Pro |
| Val | Ala | Trp | Ser | Leu | Ser |
| Cys | Glu | Leu | Phe | Phe | Tyr |
| Ala | Met | Phe | Pro | Phe | Leu |
| Phe | Ala | Phe | Phe | Thr | Lys |
| Val | Arg | Thr | Asp | Arg | Leu |
| Trp | Arg | Trp | Ala | Ala | Ala |
| Val | Ser | Val | Ala | Ala | Val |
| Ser | Ile | Pro | Leu | Val | Ala |
| Leu | Leu | Leu | Pro | Ala | Ser |
| Pro | Pro | Leu | Pro | Trp | Asp |
| Pro | Asp | Met | Pro | Gln | Leu |
| Arg | Trp | Trp | Phe | Ile | Tyr |
| Met | Phe | Pro | Pro | Val | Arg |
| Leu | Leu | Glu | Phe | Val | Leu |

-continued

| | | | | | |
|---|---|---|---|---|---|
| Gly | Met | Leu | Met | Ala | Gln |
| Ile | Val | Ile | Arg | Gly | Arg |
| Trp | Arg | Gly | Pro | Arg | Pro |
| Leu | Ala | Cys | Val | Ala | Leu |
| Phe | Ser | Ala | Val | Phe | Ala |
| Val | Thr | Phe | Ala | Val | Pro |
| Asn | His | Tyr | Asp | Pro | Gly |
| Ala | Leu | Thr | Val | Pro | Val |
| Ile | Ala | Leu | Leu | Leu | Ala |
| Ser | Val | Ala | Val | Gly | Asp |
| Val | Arg | Gly | Val | Arg | Ser |
| Trp | Leu | Gly | Thr | Arg | Thr |
| Met | Val | Leu | Leu | Gly | Glu |
| Leu | Thr | Phe | Ala | Phe | Tyr |
| Leu | Val | His | Tyr | Leu | Ile |
| Ile | Gln | Tyr | Gly | His | Arg |
| Phe | Ala | Gly | Gly | Lys | Gln |
| Gly | Tyr | Tyr | Arg | Gln | Trp |
| Asp | Thr | Pro | Ala | Ala | Val |
| Gly | Leu | Thr | Leu | Leu | Ala |
| Phe | Thr | Leu | Ala | Leu | Gly |
| Leu | Ser | Ala | Phe | Leu | His |
| Phe | Phe | Val | Glu | Lys | Pro |
| Val | Met | Arg | Thr | Leu | Gly |
| Arg | Pro | Arg | Arg | Ser | Pro |
| Asp | Ala | Gly | Ser | Thr | Pro |
| Arg | Ser | Glu | Pro | Ala | Pro |
| Ser | Gly | Thr | Pro | | | and a DNA portion coding for the following amino acid sequence

| | | | | | |
|---|---|---|---|---|---|
| Met | His | Ser | Ile | Pro | Cys |
| Gly | Ser | Lys | Pro | Ser | Ala |
| Ser | Met | Trp | Asp | Thr | Gly |
| Val | His | Asp | Asp | Phe | Asp |
| Thr | His | Ile | Ser | Glu | Thr |
| Cyc | Ser | Glu | Leu | Phe | Ser |
| Ser | Leu | Arg | Arg | Ala | Asp |
| Gln | Arg | Lys | Arg | Gly | Glu |
| Gln | Tyr | Val | Arg | Gly | Leu |
| Leu | Thr | Ala | Gln | Gly | Arg |
| Lys | Thr | Ala | Arg | Asn | Leu |
| Ala | Ala | Phe | Val | Gly | Glu |
| Gly | Ala | Ala | Asp | Gln | Asn |
| Leu | His | His | Phe | Val | Ala |
| Gly | Ser | Thr | Trp | Asp | Trp |
| Arg | Ser | Val | Arg | Ala | Ala |
| Leu | Ala | Arg | Tyr | Ala | Asp |
| Gln | Thr | Val | Arg | Gly | Asp |
| Ala | Trp | Val | Ile | Arg | Pro |
| Met | Val | Val | Tyr | Lys | Ala |
| Gly | Gly | Arg | Ser | Val | Gly |
| Val | Gly | Arg | Arg | Phe | Val |
| Pro | Asp | Leu | Gly | Arg | Val |
| Val | Ser | Cys | Gln | Gln | Ser |
| Tyr | Gly | Leu | Trp | Leu | Ala |
| Ser | Asp | Ala | Met | Ser | Ala |
| Pro | Val | Asn | Trp | His | Leu |
| Thr | Leu | Gly | Gly | Gly | Pro |
| Gly | Asp | Arg | His | Asp | Arg |
| Gln | Leu | Ser | Ala | Tyr | Gly |
| Glu | Glu | Glu | Lys | Leu | Val |
| Asp | Leu | Val | Ala | Glu | Leu |
| Thr | Arg | Ser | Asn | Arg | Val |
| Leu | Ala | Arg | Pro | Val | Val |
| Met | Asp | Ala | Arg | Ile | Ala |
| Thr | Leu | Pro | Arg | Leu | Val |
| Arg | Ala | Leu | Ser | Ala | Ala |
| Asp | Gln | Ser | Phe | Leu | Leu |
| Arg | Val | Ser | Gly | Asp | Leu |
| Pro | Leu | Ala | Leu | Ala | Gly |
| Ser | Arg | Gly | Gln | Leu | Asp |
| Arg | Arg | Ala | Gln | Val | Trp |
| Pro | Ala | Gln | His | Leu | Met |
| Glu | Gln | Leu | Lys | Arg | Leu |
| Arg | Arg | Pro | Val | Glu | Trp |
| Gln | Gly | Ser | Ile | Ser | Phe |
| Val | Ala | Pro | Cys | Asn | Val |
| Val | Leu | Thr | Asp | Gln | Leu |
| Pro | Gln | Arg | Thr | Leu | Leu |
| Leu | Phe | Gly | Val | Trp | Arg |
| Ala | Asn | Arg | Arg | Arg | Pro |
| Ala | Asp | Leu | Trp | Lue | Thr |
| Asp | Lue | Thr | Ser | Trp | Asn |
| Arg | Gly | Ala | Leu | Leu | Arg |
| Leu | Ala | Met | Leu | Thr | Cys |
| Arg | Val | Asp | Ala | Asp | Phe |
| Ala | Arg | Val | Ser | Leu | Gly |
| Val | Gly | Ile | Arg | Asp | Phe |
| Glu | Gly | Arg | Ser | Phe | Gln |
| Gly | Trp | His | Arg | His | Val |
| Thr | Leu | Ala | Ser | Ile | Ala |
| His | Ala | Leu | Arg | Leu | Ser |
| Cys | Thr | Asp | Thr | Ala | Arg |
| Thr | Pro | Thr | Ala | Pro | Ala |
| Leu | Ser | Arg. | | | |

6. The DNA fragment and the DNA restriction fragment according to claim 1 which have the following base sequence

```
  1
GATCACACTC TTCGAGGAAC
TCCACGGGCG CTGACGCACG
CGGCGAGGGC GCGCCCCGCA
CCGGTCGTCC CGCGTCGGCT
                   100
ACGGAGTGCC GGACGGGGCG
GGTTCGGACC TGGGTGTCGA
GCCGGCGTCC GGGGACCGCC
GCGGCCGTCC CAGGGTTCGC
ATGACCGGCT TCTCCACGAA
                   200
GAAGTGCAGG AACGCCGACA
GCCCCAGCGC CAGCGTGAAG
GCGAGCAGGG TCAGCCCGAC
GGCGGCCGGT GTGTCCACT
GCCGGTAATA GCCCTGCTTC
                   300
CCGCCGGCGA AGCGGTGCCC
GTACTGGATG ATCAGGTAGT
GCACGAGGTA GAAGGCGAAG
GTGAGTTCCC CCAGCAGCAC
CATCGTCCTG GTCCCCAGCC
                   400
AGGAGCGGAC GCCGCGCACA
TCACCGACGG CCACCGAGGC
GAGCAGCAGC GCGATCACCG
GGACGGTCAA CGCGCCGGGG
TCGTAGTGGT TCGGCACCGC
                   500
GAACGTCACC GCGAACACCG
CTGAGAACAG CGCGACGCAG
GCCAGGGGAC GCGGGCCCCT
CCAGCGTCCC CGGATCACGA
TCTGGGCCAT GAGCATCCCG
                   600
AGCACGAACT CCAGCAGCCG
CACCGGCGGG AACATGTAGA
TGAACCACCA CCGCAGCTGC
GGCATGTCCG GGTCCCACGG
CAGGGCGGG CTGGCCGGCA
                   700
GCAGCAGTGC GACCAGGGGG
ATGGAGACGG CGGCCACGGA
CACCGCGGCG GCCCACCGCC
AGAGCCGGTC CGTACGGACC
TTGGTGAAGA AGGCGAAGAG
                   800
GAACGGGAAC ATGGCGTAGA
AGAACAGCTC GCAGGAGAGC
GACCACGCCA CCGGGTTCAT
GCTGCCGTAC TCGTGGTGGT
CGGGGAACCA TGCCTGGATC
                   900
AGCAGCAGGT TCGTGAGCAG
TCCGTCCCAC ACCGATCGGC
CCATGTTGGG CTCGTTGAGG
GCCAGCACGA TCAGCAGCGT
```

-continued

```
CACCAGCAGC ACGGGCAGGT
                      1000
GCAGCGAGTA CGCGCGGACC
GTGCGCCGCC GCCAGAAGTT
CACCTTGGAC TTGTCGGGCA
GACCCGCCCA GGTGAGGACG
AAACCGCTGA GCATGAAGAA
                      1100
GAACGAGACC GTCAGCGGGC
CCAGCCGGTT CAGCGGGAAC
TGCAGCGCGG AATTGATCTC
GGTGTTCTTG AAGAACGGCT
GTGTCGATAT ATGGGAGGTG
                      1200
AATACCAGTA GAGCGGAGAT
GAAACGCATC CCGCCGAGCG
CGGGAAGATG TTTCGGCAGG
GGCATGGGTG ACCTCGCGGC
GGACGGGTGG GTGGGAGCAG
                      1300
ATGTCTAAGG CACCGCGCGG
CCGCCGGGCA AGGCGTATCT
GACAAAGAGT GTGAGCCGCC
GCGCGACAGT GGTGTGTTCC
CACCGCTGCA CGGCCGGCGA
                      1400
CGGTGGTTTC GTCACCGGGC
GACGCGGATT TAATCATCCG
GAAACACGGA CGACGGTTCT
TCGCGGCGGT GTGACGCGAG
GTGTGCGGGA AGAATTGTGT
                      1500
GGCCTCGGCA CCTGGATTTA
CGGAACGAAT TAACTGAGGC
TGGCCAGCAG GTCTTTTCCA
GTGGATCAAG CGGCTTGTGA
GGGTCATAGT GCACAGTATT
                      1600
CCGTGTGGCT CAAAACCGTC
GGCCTCCATG TGGGACACCG
GTGTCCATGA CGACTTCGAT
ACGCACATCT CCGAGACCTG
CTCGGAGCTG TTCAGTTCGC
                      1700
TGCGCCGGGC CGACCAGCGC
AAGAGGGGCG AACAGTACGT
CCGTGGTCTG CTCACCGCTC
AGGGACGCAA GACCGCCCGC
AACCTCGCCG CGTTCGTCGG
                      1800
TGAAGGCGCC GCGGACCAGA
ACCTCCACCA CTTCGTGGCC
GGATCCACCT GGGACTGGCG
CTCCGTGCGT GCCGCGCTGG
CCCGCTACGC CGACCAGACG
                      1900
GTACGCGGGG ACGCGTGGGT
GATCCGCCCC ATGGTGGTCT
ACAAGGCAGG GGGACGGTCG
GTCGGCGTGG GCCGGCGCTT
CGTACCCGAC CTGGGGCGGG
                      2000
TGGTCAGCTG TCAGCAGAGC
TACGGGCTCT GGCTCGCCTC
CGACGCCATG TCGGCACCGG
TGAACTGGCA TCTGACGCTG
```

```
GGCGGCGGAC CGGGCGACCG
                      2100
TCACGATCGG CAGCTGAGCG
CGTACGGCGA GGAGGAGAAG
CTCGTCGACC TGGTGGCGGA
ACTCACGCGC TCGAACCGGG
TGTTGGCGCG TCCGGTGGTG
                      2200
ATGGACGCGC GGATCGCCAC
GCTGCCCCGG CTGGTTCGGG
CGCTGTCCGC GGCTGATCAA
TCGTTTCTCT TAAGGGTGAG
CGGCGATCTT CCGCTCGCCC
                      2300
TCGCCGGCAG CCGGGGCCAA
CTGGACAGGC GCGCGCAGGT
CTGGCCCGCC CAGCACCTCA
TGGAACAGCT CAAGCGGCTC
AGGCGCCCTG TGGAGTGGCA
                      2400
GGGCTCCATC AGCTTCGTCG
CCCCGTGCAA CGTGGTGCTG
ACCGATCAGC TGCCGCAGCG
CACGCTCCTG CTGTTCGGGG
TGTGGCGCGC CAACCGCAGG
                      2500
CGACCCGCGG ACCTGTGGCT
CACCGACCTC ACGTCCTGGA
ACCGCGGCGC ACTGCTGCGG
CTGGCCATGC TGACCTGCCG
CGTGGACGCC GACTTCGCCC
                      2600
GCGTCAGCCT GGGCGTCGGC
ATCCGCGACT TCGAGGGCCG
CTCCTTCCAG GGCTGGCACC
GTCACGTGAC ACTGGCCTCG
ATAGCCCACG CCCTACGCCT
                      2700
TTCCTGCACC GACACCGCCC
GCACCCCCAC GGCCCCGGCC
CTGTCCCGCT GACGGTGAGG
TCACGGGGC.
```

7. A plasmid containing the DNA fragment of any one of claim 1, 4, 5, or 6, which is a recombinant plasmid resulting from insertion of said DNA fragment into a vector plasmid selected from pIJ702, pIJ943, pIJ350 and pUC18.

8. The plasmid of claim 7 which is pMAB1.

9. A microorganism transformed with the plasmid set forth in any one of claim s 7 or 8, said microorganism being of the genus *Streptomyces* or of the species *E. coli*.

10. The microorganism of claim 9 in which the host organism is *Streptomyces lividans* TK24 or *Streptomyces fradiae* ATCC 19609.

11. The microorganism of claim 9 in which the host microorganism is a macrolide antibiotic with a mycarose substituent producing microorganism which does not substantially produce an enzyme capable of acylating the 4"-position of a macrolide antibiotic.

12. The microorganism set forth in claim 11 in which the macrolide antibiotic-producing microorganism is *Streptomyces fradiae* ATCC 19609.

* * * * *